(12) United States Patent
Bardy

(10) Patent No.: US 7,972,274 B2
(45) Date of Patent: ***Jul. 5, 2011

(54) SYSTEM AND METHOD FOR ANALYZING A PATIENT STATUS FOR CONGESTIVE HEART FAILURE FOR USE IN AUTOMATED PATIENT CARE

(75) Inventor: Gust H. Bardy, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 661 days.

This patent is subject to a terminal disclaimer.

(21) Appl. No.: 10/876,118

(22) Filed: Jun. 24, 2004

(65) Prior Publication Data

US 2004/0230127 A1 Nov. 18, 2004

Related U.S. Application Data

(60) Division of application No. 10/042,402, filed on Jan. 7, 2002, now Pat. No. 6,811,537, which is a continuation of application No. 09/441,623, filed on Nov. 16, 1999, now Pat. No. 6,336,903.

(51) Int. Cl.
*A61B 5/0402* (2006.01)
(52) U.S. Cl. ........................................ 600/508
(58) Field of Classification Search .................. 600/508, 600/513; 128/920, 923, 924, 925
See application file for complete search history.

(56) References Cited

U.S. PATENT DOCUMENTS

| | | | |
|---|---|---|---|
| 3,837,339 A | 9/1974 | Aisenberg et al. | |
| 4,142,533 A | 3/1979 | Brownlee et al. | |
| 4,197,856 A | 4/1980 | Northrop | |
| 4,428,378 A | 1/1984 | Anderson et al. | |
| 4,531,527 A | 7/1985 | Reinhold, Jr. et al. | |
| 4,566,461 A | 1/1986 | Lubell et al. | |
| 4,686,999 A | 8/1987 | Snyder et al. | |
| 4,803,625 A * | 2/1989 | Fu et al. | 600/483 |
| 4,809,697 A | 3/1989 | Causey, III et al. | |
| 4,852,570 A | 8/1989 | Levine | |
| 4,899,758 A * | 2/1990 | Finkelstein et al. | 600/485 |
| 4,958,645 A | 9/1990 | Cadell et al. | |
| 4,974,607 A | 12/1990 | Miwa | |
| 4,987,897 A | 1/1991 | Funke | |

(Continued)

FOREIGN PATENT DOCUMENTS

EP 0 34 2859 11/1989

(Continued)

OTHER PUBLICATIONS

Merriam Webster Online and Dictionary.com definitions for "implantable". Sep. 30, 2007.*

(Continued)

*Primary Examiner* — George R Evanisko
(74) *Attorney, Agent, or Firm* — Pauly, DeVries Smith & Deffner, L.L.C.

(57) ABSTRACT

A system and method for providing diagnosis and monitoring of congestive heart failure for use in automated patient care is described. At least one recorded physiological measure is compared to at least one other recorded physiological measure on a substantially regular basis to quantify a change in patient pathophysiological status for equivalent patient information. An absence, an onset, a progression, a regression, and a status quo of congestive heart failure is evaluated dependent upon the change in patient pathophysiological status.

19 Claims, 23 Drawing Sheets

U.S. PATENT DOCUMENTS

| | | | |
|---|---|---|---|
| 5,040,536 A | 8/1991 | Riff | |
| 5,113,859 A | 5/1992 | Funke | |
| 5,113,869 A | 5/1992 | Nappholz et al. | |
| 5,133,346 A | 7/1992 | Kulkarni | |
| 5,178,149 A | 1/1993 | Imburgia et al. | |
| 5,199,428 A | 4/1993 | Obel et al. | |
| 5,301,105 A | 4/1994 | Cummings, Jr. | |
| 5,307,263 A | 4/1994 | Brown | |
| 5,309,919 A | 5/1994 | Snell et al. | |
| 5,313,593 A | 5/1994 | Barakat et al. | |
| 5,331,549 A | 7/1994 | Crawford, Jr. | |
| 5,336,245 A | 8/1994 | Adams et al. | |
| 5,355,889 A | 10/1994 | Nevo et al. | |
| 5,357,427 A | 10/1994 | Langen et al. | |
| 5,390,238 A | 2/1995 | Kirk et al. | |
| 5,416,695 A | 5/1995 | Stutman et al. | |
| 5,421,343 A | 6/1995 | Feng | |
| 5,437,278 A | 8/1995 | Wilk | |
| 5,438,983 A | 8/1995 | Falcone | |
| 5,464,012 A | 11/1995 | Falcone | |
| 5,544,661 A | 8/1996 | Davis et al. | |
| 5,553,609 A | 9/1996 | Chen et al. | |
| 5,557,514 A | 9/1996 | Seare et al. | |
| 5,576,952 A | 11/1996 | Stutman | |
| 5,584,868 A | 12/1996 | Salo et al. | |
| 5,591,215 A | 1/1997 | Greenhut et al. | |
| 5,603,331 A | 2/1997 | Heemels et al. | |
| 5,660,183 A | 8/1997 | Chiang et al. | |
| 5,673,691 A | 10/1997 | Abrams et al. | |
| 5,687,734 A | 11/1997 | Dempsey et al. | |
| 5,697,959 A | 12/1997 | Poore | |
| 5,704,345 A | 1/1998 | Berthon-Jones | |
| 5,704,366 A | 1/1998 | Tracklind et al. | |
| 5,711,297 A | 1/1998 | Iliff | |
| 5,713,350 A | 2/1998 | Yokota et al. | |
| 5,720,770 A | 2/1998 | Nappholz et al. | |
| 5,720,771 A | 2/1998 | Snell | |
| 5,724,580 A * | 3/1998 | Levin et al. | 707/104.1 |
| 5,724,983 A * | 3/1998 | Selker et al. | 600/301 |
| 5,738,102 A | 4/1998 | Lemelson | |
| 5,743,267 A | 4/1998 | Nikolic | |
| 5,749,907 A | 5/1998 | Mann | |
| 5,749,908 A | 5/1998 | Snell | |
| 5,752,976 A | 5/1998 | Duffin et al. | |
| 5,769,074 A | 6/1998 | Barnhill et al. | |
| 5,772,586 A | 6/1998 | Heinonen et al. | |
| 5,772,599 A | 6/1998 | Nevo et al. | |
| 5,772,604 A | 6/1998 | Langberg et al. | |
| 5,778,882 A | 7/1998 | Raymond et al. | |
| 5,785,650 A | 7/1998 | Akasaka et al. | |
| 5,785,660 A | 7/1998 | Van Lake et al. | |
| 5,788,640 A | 8/1998 | Peters | |
| 5,788,643 A * | 8/1998 | Feldman | 600/506 |
| 5,792,062 A | 8/1998 | Poon et al. | |
| 5,819,251 A | 10/1998 | Kremer et al. | |
| 5,855,593 A | 1/1999 | Olson et al. | |
| 5,860,918 A | 1/1999 | Schradi et al. | |
| 5,876,353 A | 3/1999 | Riff | |
| 5,879,375 A | 3/1999 | Larson, Jr. et al. | |
| 5,891,178 A | 4/1999 | Mann et al. | |
| 5,897,493 A | 4/1999 | Brown | |
| 5,911,132 A | 6/1999 | Sloane | |
| 5,931,857 A | 8/1999 | Prieve et al. | |
| 5,954,640 A | 9/1999 | Szabo | |
| 5,957,861 A | 9/1999 | Combs et al. | |
| 5,974,124 A | 10/1999 | Schlueter, Jr. et al. | |
| 5,987,352 A | 11/1999 | Klein et al. | |
| 5,993,386 A | 11/1999 | Ericsson | |
| 6,004,276 A | 12/1999 | Wright et al. | |
| 6,014,581 A | 1/2000 | Whayne et al. | |
| 6,024,699 A | 2/2000 | Surwit et al. | |
| 6,038,469 A | 3/2000 | Karlsson et al. | |
| 6,047,203 A | 4/2000 | Sackner et al. | |
| 6,050,940 A | 4/2000 | Braun | |
| 6,063,028 A | 5/2000 | Luciano | |
| 6,067,466 A | 5/2000 | Selker | |
| 6,073,046 A | 6/2000 | Patel | |
| 6,080,106 A | 6/2000 | Lloyd et al. | |
| 6,083,248 A | 7/2000 | Thompson | |
| 6,093,146 A | 7/2000 | Filangeri | |
| 6,095,985 A | 8/2000 | Raymond et al. | |
| 6,102,856 A | 8/2000 | Groff et al. | |
| 6,122,351 A | 9/2000 | Schlueter, Jr. et al. | |
| 6,129,675 A | 10/2000 | Jay | |
| 6,135,951 A | 10/2000 | Richardson et al. | |
| 6,139,494 A * | 10/2000 | Cairnes | 600/300 |
| 6,152,882 A | 11/2000 | Prutchi | |
| 6,155,267 A | 12/2000 | Nelson | |
| 6,168,563 B1 | 1/2001 | Brown | |
| 6,168,653 B1 | 1/2001 | Myers | |
| 6,171,237 B1 * | 1/2001 | Avitall et al. | 600/300 |
| 6,171,256 B1 | 1/2001 | Joo et al. | |
| 6,203,495 B1 | 3/2001 | Bardy | |
| 6,221,011 B1 | 4/2001 | Bardy | |
| 6,223,078 B1 | 4/2001 | Marcovecchio | |
| 6,225,901 B1 | 5/2001 | Kail, IV | |
| 6,234,964 B1 | 5/2001 | Iliff | |
| 6,246,992 B1 | 6/2001 | Brown | |
| 6,249,705 B1 | 6/2001 | Snell | |
| 6,250,309 B1 | 6/2001 | Krichen et al. | |
| 6,261,230 B1 | 7/2001 | Bardy | |
| 6,263,245 B1 | 7/2001 | Snell | |
| 6,270,457 B1 | 8/2001 | Bardy | |
| 6,277,072 B1 | 8/2001 | Bardy | |
| 6,280,380 B1 | 8/2001 | Bardy | |
| 6,283,923 B1 | 9/2001 | Finkelstein et al. | |
| 6,287,252 B1 | 9/2001 | Lugo | |
| 6,290,646 B1 | 9/2001 | Cosentino et al. | |
| 6,302,844 B1 | 10/2001 | Walker | |
| 6,306,088 B1 | 10/2001 | Krausman et al. | |
| 6,312,378 B1 | 11/2001 | Bardy | |
| 6,331,160 B1 | 12/2001 | Bardy | |
| 6,336,900 B1 | 1/2002 | Alleckson | |
| 6,336,903 B1 * | 1/2002 | Bardy | 600/508 |
| 6,361,501 B1 | 3/2002 | Amano et al. | |
| 6,363,282 B1 | 3/2002 | Nichols et al. | |
| 6,368,284 B1 | 4/2002 | Bardy | |
| 6,379,301 B1 | 4/2002 | Worthington et al. | |
| 6,398,728 B1 | 6/2002 | Bardy | |
| 6,411,840 B1 | 6/2002 | Bardy | |
| 6,416,471 B1 | 7/2002 | Kumar | |
| 6,428,483 B1 | 8/2002 | Carlebach | |
| 6,440,066 B1 | 8/2002 | Bardy | |
| 6,442,432 B2 | 8/2002 | Lee | |
| 6,442,433 B1 | 8/2002 | Linberg | |
| 6,454,705 B1 * | 9/2002 | Cosentino et al. | 600/300 |
| 6,454,707 B1 * | 9/2002 | Casscells et al. | 600/300 |
| 6,473,646 B2 | 10/2002 | Sun et al. | |
| 6,477,424 B1 | 11/2002 | Thompson et al. | |
| 6,478,737 B2 | 11/2002 | Bardy | |
| 6,480,745 B2 | 11/2002 | Nelson et al. | |
| 6,497,655 B1 | 12/2002 | Linberg et al. | |
| 6,512,949 B1 | 1/2003 | Combs et al. | |
| 6,524,239 B1 | 2/2003 | Reed et al. | |
| 6,564,104 B2 | 5/2003 | Nelson et al. | |
| 6,648,820 B1 | 11/2003 | Sarel | |
| 6,662,032 B1 | 12/2003 | Gavish et al. | |
| 6,811,537 B2 | 11/2004 | Bardy | |
| 6,827,670 B1 | 12/2004 | Stark et al. | |
| 6,908,437 B2 * | 6/2005 | Bardy | 600/508 |
| 6,920,360 B2 | 7/2005 | Lee et al. | |
| 7,104,955 B2 | 9/2006 | Bardy | |
| 7,134,996 B2 | 11/2006 | Bardy | |
| 2001/0023360 A1 | 9/2001 | Nelson et al. | |
| 2001/0039375 A1 | 11/2001 | Lee et al. | |
| 2003/0055679 A1 | 3/2003 | Soll et al. | |

FOREIGN PATENT DOCUMENTS

| | | |
|---|---|---|
| EP | 0342859 | 11/1989 |
| EP | 0 513 457 | 11/1992 |
| EP | 0513457 | 11/1992 |
| EP | 0 531 889 | 3/1993 |
| EP | 0531889 | 3/1993 |
| EP | 0 711 531 | 5/1996 |
| EP | 0711531 | 5/1996 |
| EP | 0887759 | 12/1998 |
| WO | WO 97/39792 | 10/1997 |

| | | |
|---|---|---|
| WO | WO-9739792 | 10/1997 |
| WO | WO-9801742 | 1/1998 |
| WO | WO 98/01742 | 2/1998 |
| WO | WO 98/42103 | 9/1998 |
| WO | WO-99/14882 | 3/1999 |
| WO | WO 99/46718 | 9/1999 |
| WO | WO-9946718 | 9/1999 |
| WO | WO 99/55226 | 11/1999 |
| WO | WO-99/55226 | 11/1999 |

OTHER PUBLICATIONS

Moody GB, "Integration of Real-Time and Off-Line Clinical Data in the MIMIC Database," Computers in Cardiology 1997 vol. 24, pp. 585-588, Cambridge, MA USA.

Long WJ, et al., "Differential Diagnosis Generation From a Causal Network With Probabilities," Computers in Cardiology, 1988, Proceedings, pp. 185-188, Washington DC, USA.

Dunn et al., "Telemedicine Links Patients in Sioux Lookout with Doctors in Toronto," CMA Journal, vol. 122, pp. 484-487 (Feb. 23, 1980).

Auer et al., "Paced Epimyocardial Electrograms for Noninvasive Rejection Monitoring After Heart Transplantation," The Journal of Heart and Lung Transplantation, vol. 15, No. 10, pp. 993-998 (Oct. 1996).

Schreier et al., "A Non-Invasive Rejection Monitoring System Based on Remote Analysis of Intramyocardial Electrograms from Heart Transplants," IEEE, pp. 35-36 (1997).

Roberge et al., "Basic and Applied Biomedical Engineering Building Blocks for Health Care," 1995 IEEE Engineering in Medicine and Biology 17$^{th}$ Annual Conference, vol. 1, Montreal-Canada, (Sep. 20-23, 1995).

Hutten et al., "Cardiac Telemonitoring by Integrating Pacemaker Telemetry within Worldwide Data Communication Systems," Proceedings of 19$^{th}$ International Conference, IEEE/EMBS, Chicago, IL, pp. 974-976 (Oct. 30-Nov. 2, 1997).

Vargas, Juan E., "Home-Based Monitoring of Cardiac Patients," Dept. of Electr. & Comput. Eng., South Carolina Univ., Columbia, SC, Information Technology Applications in Biomedicine, Proceedings., 1998 IEEE International Conference, pp. 133-136 (May 16-17, 1998).

Magrabi et al., "Web Based Longitudinal ECG Monitoring," Proceedings of 20$^{th}$ Annual International Conference of the IEEE Engineering in Medicine and Biology Society, vol. 20, No. 3, pp. 1155-1158 (1998).

Nelwan et al., "Ubiquitous Access to Real-Time Patient Monitoring Data," Computers in Cardiollogy., vol. 24, pp. 271-274 (1997).

Office Actions, Responses, and Appeal-related documents for EP Patent Application No. 00650193.6, filed Nov. 16, 2000, which corresponds to U.S. Appl. No. 09/441,623, which is the parent application to the present application(U.S. Appl. No. 10/876,118) (113 pages).

Examiner's First Report of AU Patent Application No. 2002302016, dated Jun. 22, 2005, which corresponds to U.S. Appl. No. 09/441,623, which is the parent application to the present application(U.S. Appl. No. 10/876,118) (2 pages).

Partial File History (Office Actions and Responses from Nov. 5, 2009 to Nov. 27, 2009) for co-pending U.S. Appl. No. 11/150,334, "System and Method for Diagnosing and Monitoring Congestive Heart Failure," which claims priority to the same parent application (U.S. Appl. No. 09/441,623) as the present application (U.S. Appl. No. 10/876,118) (18 pages).

Amendment and Response dated Mar. 1, 2010 for co-pending U.S. Appl. No. 11/150,334, "System and Method for Diagnosing and Monitoring Congestive Heart Failure," which claims priority to the same parent application (U.S. Appl. No. 09/441,623) as the present application (U.S. Appl. No. 10/876,118) (13 pages).

File History for Canadian Patent Application No. 2325660 (abandoned) which corresponds to U.S. Appl. No. 09/441,623, filed Nov. 16, 1999, which is the parent application to the present U.S. Appl. No. 10/876,118 (17 pages).

Belardinelli et al., "A Four-Minutes Submaximal Constant Work Rate Exercise Test to Assess Cardiovascular Functional Class in Chronic Heart Failure", The American Journal of Cardiology, 81:1210-1214 (1998).

Discovery® II Pacemaker System Guide Manual, Dec. 2003 (207 pages).

Discovery™ II Pacemaker Physician's Technical Manual, Oct. 1999 (6 pages).

Medtronic GEM® 7227Cx, 7227B, 7227D, 7227E Implantable Cardioverter Defibrillators, Sep. 2001 (313 pages).

Medtronic GEM® II DR 7273 Dual Chamber Implantable Cardioverter Defibrillator 9964E Software, Jan. 2001 (402 pages).

Operators Manual for the Model 2901 Portable Programmer Recorder Monitor by Guidant, Jan. 1999 (22 pages).

Office Actions, Responses and Allowance-related documents for EP Patent Application No. 00202604.05, filed Jul. 20, 2000, which corresponds to U.S. Appl. No. 09/361,332, which is the parent application to the co-pending U.S. Appl. No. 11/635,364 (40 pages).

EP Search Report for EP Patent Application No. 00202604.05, dated Dec. 8, 2000, which corresponds to U.S. Appl. No. 09/361,332, which is the parent application to the co-pending U.S. Appl. No. 11/635,364 (2 pages).

File History (as of Jul. 22, 2010) for co-pending U.S. Appl. No. 11/102,522, filed Apr. 8, 2005 which is abandoned, entitled "System and Method for Determining a Reference Baseline Record" (409 pages).

Partial File History (from Mar. 2, 2010 to Jul. 22, 2010) for co-pending U.S. Appl. No. 11/150,334, filed Jun. 10, 2005, entitled "System and Method for Diagnosing and Monitoring Congestive Heart Failure", which claims priority to the same parent application (U.S. Appl. No. 10/042,402) as the present application (U.S. Appl. No. 10/876,118) (17 pages).

File History (as of Jul. 22, 2010) for co-pending U.S. Appl. No. 11/635,205, filed Dec. 6, 2006, entitled "System and Method for Generating Baseline Data for Automated Management of Edema" (279 pages).

File History (as of Jul. 22, 2010) for co-pending U.S. Appl. No. 11/635,364, filed Dec. 6, 2006, entitled "System and Method for Providing Baseline Data for Automated Patient Management" (290 pages).

File History (as of Jul. 22, 2010) for co-pending U.S. Appl. No. 11/880,754, filed Jul. 23, 2007, entitled "System and Method for Determining a Reference Baseline for Use in Cardiac Decompensation Assessment" (160 pages).

File History (as of Jul. 22, 2010) for co-pending U.S. Appl. No. 11/894,514, filed Aug. 20, 2007 which is abandoned, entitled "System and Method for Determining a Reference Baseline for Use in Heart Failure Assessment" (232 pages).

File History for co-pending U.S. Appl. No. 11/150,334, "System and Method for Diagnosing and Monitoring Congestive Heart Failure," (259 pages).

Braunwald, E. , "Heart-Disease—A Textbook of Cardiovascular Medicine", 1997 , pp. 452-454.

Long, W. J. et al., "Differential Diagnosis Generation From a Causal Network With Probabilities", *Computers in Cardiology* 1988 , Proceedings, pp. 185-188.

Moody, G. B. , "Integration of Real-Time and Off-Line Clinical Data in the MIMIC Database", *Computers in Cardiology* 1997 , vol. 24, pp. 585-588.

Partial File History (from Jul. 23, 2010 to Feb. 21, 2011) for co-pending U.S. Appl. No. 11/635,364, filed Dec. 6, 2006, entitled "System and Method for Providing Baseline Data for Automated Patient Management", which claims priority to the same parent application (U.S. Appl. No. 09/361,332) as the present application (U.S. Appl. No. 11/894,514) (47 pages).

Partial File History (from Jul. 23, 2010 to Feb. 21, 2011) for co-pending U.S. Appl. No. 11/894,514, filed Dec. 6, 2006, entitled "System and Method for Providing Baseline Data for Automated Patient Management", which claims priority to the same parent application (U.S. Appl. No. 09/361,332) as the present application (U.S. Appl. No. 11/894,514) (47 pages).

* cited by examiner

Fig. 6.

Patient 1

| Set 0 | |
|---|---|
| $X_0$ | • |
| $Y_0$ | • |
| $Z_0$ | • |

*time →*

Patient 2

| Set 0 | |
|---|---|
| $X_{0'}$ | • |
| $Y_{0'}$ | • |
| $Z_{0'}$ | • |

*time →*

Patient 3

| Set 0 | |
|---|---|
| $X_{0''}$ | • |
| $Y_{0''}$ | • |
| $Z_{0''}$ | • |

*time →*

SYSTEM AND METHOD FOR ANALYZING A PATIENT STATUS FOR CONGESTIVE HEART FAILURE FOR USE IN AUTOMATED PATIENT CARE

CROSS-REFERENCE TO RELATED APPLICATION

This patent application is a divisional of U.S. Ser. No. 10/042,402, filed Jan. 7, 2002 U.S. Pat. No. 6,811,537, issued Nov. 2, 2004, which is a continuation of U.S. Pat. No. 6,336,903, issued Jan. 8, 2002, the disclosures of which are incorporated herein by reference, and the priority filing dates of which are claimed.

FIELD OF THE INVENTION

The present invention relates in general to congestive heart failure (CHF) diagnosis and analysis, and, in particular, to a system and method for providing diagnosis and monitoring of congestive heart failure for use in automated patient care throughout disease absence, onset, progression, regression, and status quo.

BACKGROUND OF THE INVENTION

Presently, congestive heart failure is one of the leading causes of cardiovascular disease-related deaths in the world. Clinically, congestive heart failure involves circulatory congestion caused by heart disorders that are primarily characterized by abnormalities of left ventricular function and neurohormonal regulation. Congestive heart failure occurs when these abnormalities cause the heart to fail to pump blood at a rate required by the metabolizing tissues. The effects of congestive heart failure range from impairment during physical exertion to a complete failure of cardiac pumping function at any level of activity. Clinical manifestations of congestive heart failure include respiratory distress, such as shortness of breath and fatigue, and reduced exercise capacity or tolerance.

Several factors make the early diagnosis and prevention of congestive heart failure, as well as the monitoring of the progression of congestive heart failure, relatively difficult. First, the onset of congestive heart failure is generally subtle and erratic. Often, the symptoms are ignored and the patient compensates by changing his or her daily activities. As a result, many congestive heart failure conditions or deteriorations in congestive heart failure remain undiagnosed until more serious problems arise, such as pulmonary edema or cardiac arrest. Moreover, the susceptibility to suffer from congestive heart failure depends upon the patient's age, sex, physical condition, and other factors, such as diabetes, lung disease, high blood pressure, and kidney function. No one factor is dispositive. Finally, annual or even monthly checkups provide, at best, a "snapshot" of patient wellness and the incremental and subtle clinicophysiological changes which portend the onset or progression of congestive heart failure often go unnoticed, even with regular health care. Documentation of subtle improvements following therapy, that can guide and refine further evaluation and therapy, can be equally elusive.

Nevertheless, taking advantage of frequently and regularly measured physiological measures, such as recorded manually by a patient, via an external monitoring or therapeutic device, or via implantable device technologies, can provide a degree of detection and prevention heretofore unknown. For instance, patients already suffering from some form of treatable heart disease often receive an implantable pulse generator (IPG), cardiovascular or heart failure monitor, therapeutic device, or similar external wearable device, with which rhythm and structural problems of the heart can be monitored and treated. These types of devices are useful for detecting physiological changes in patient conditions through the retrieval and analysis of telemetered signals stored in an onboard, volatile memory. Typically, these devices can store more than thirty minutes of per heartbeat data recorded on a per heartbeat, binned average basis, or on a derived basis from, for example, atrial or ventricular electrical activity, minute ventilation, patient activity score, cardiac output score, mixed venous oxygen score, cardiovascular pressure measures, and the like. However, the proper analysis of retrieved telemetered signals requires detailed medical subspecialty knowledge, particularly by cardiologists and cardiac electrophysiologists.

Alternatively, these telemetered signals can be remotely collected and analyzed using an automated patient care system. One such system is described in a related, commonly owned U.S. Pat. No. 6,312,378, issued Nov. 6, 2001, the disclosure of which is incorporated herein by reference. A medical device adapted to be implanted in an individual patient records telemetered signals that are then retrieved on a regular, periodic basis using an interrogator or similar interfacing device. The telemetered signals are downloaded via an internetwork onto a network server on a regular, e.g., daily, basis and stored as sets of collected measures in a database along with other patient care records. The information is then analyzed in an automated fashion and feedback, which includes a patient status indicator, is provided to the patient.

While such an automated system can serve as a valuable tool in providing remote patient care, an approach to systematically correlating and analyzing the raw collected telemetered signals, as well as manually collected physiological measures, through applied cardiovascular medical knowledge to accurately diagnose the onset of a particular medical condition, such as congestive heart failure, is needed. One automated patient care system directed to a patient-specific monitoring function is described in U.S. Pat. No. 5,113,869 ('869) to Nappholz et al. The '869 patent discloses an implantable, programmable electrocardiography (ECG) patient monitoring device that senses and analyzes ECG signals to detect ECG and physiological signal characteristics predictive of malignant cardiac arrhythmias. The monitoring device can communicate a warning signal to an external device when arrhythmias are predicted. However, the Nappholz device is limited to detecting tachycardias. Unlike requirements for automated congestive heart failure monitoring, the Nappholz device focuses on rudimentary ECG signals indicative of malignant cardiac tachycardias, an already well-established technique that can be readily used with onboard signal detection techniques. Also, the Nappholz device is patient specific only and is unable to automatically take into consideration a broader patient or peer group history for reference to detect and consider the progression or improvement of cardiovascular disease. Moreover, the Nappholz device has a limited capability to automatically self-reference multiple data points in time and cannot detect disease regression even in the individual patient. Also, the Nappholz device must be implanted and cannot function as an external monitor. Finally, the Nappholz device is incapable of tracking the cardiovascular and cardiopulmonary consequences of any rhythm disorder.

Consequently, there is a need for a systematic approach to detecting trends in regularly collected physiological data indicative of the onset, progression, regression, or status quo of congestive heart failure diagnosed and monitored using an automated, remote patient care system. The physiological data could be telemetered signals data recorded either by an external or an implantable medical device or, alternatively, individual measures collected through manual means. Preferably, such an approach would be capable of diagnosing both acute and chronic congestive heart failure conditions, as well as the symptoms of other cardiovascular diseases. In addition, findings from individual, peer group, and general population patient care records could be integrated into continuous, ongoing monitoring and analysis.

SUMMARY OF THE INVENTION

The present invention provides a system and method for diagnosing and monitoring the onset, progression, regression, and status quo of congestive heart failure using an automated collection and analysis patient care system. Measures of patient cardiovascular information are either recorded by an external or implantable medical device, such as an IPG, cardiovascular or heart failure monitor, or therapeutic device, or manually through conventional patient-operable means. The measures are collected on a regular, periodic basis for storage in a database along with other patient care records. Derived measures are developed from the stored measures. Select stored and derived measures are analyzed and changes in patient condition are logged. The logged changes are compared to quantified indicator thresholds to detect findings of respiratory distress or reduced exercise capacity indicative of the two principal cardiovascular pathophysiological manifestations of congestive heart failure: elevated left ventricular end diastolic pressure and reduced cardiac output, respectively.

An embodiment of the present invention is an automated system and method for diagnosing and monitoring congestive heart failure and outcomes thereof. A plurality of monitoring sets is retrieved from a database. Each of the monitoring sets includes recorded measures relating to patient information recorded on a substantially continuous basis. A patient status change is determined by comparing at least one recorded measure from each of the monitoring sets to at least one other recorded measure. Both recorded measures relate to the same type of patient information. Each patient status change is tested against an indicator threshold corresponding to the same type of patient information as the recorded measures that were compared. The indicator threshold corresponds to a quantifiable physiological measure of a pathophysiology indicative of congestive heart failure.

A further embodiment is an automated collection and analysis patient care system and method for diagnosing and monitoring congestive heart failure and outcomes thereof. A plurality of monitoring sets is retrieved from a database. Each monitoring set includes recorded measures that each relates to patient information and include either medical device measures or derived measures calculable therefrom. The medical device measures are recorded on a substantially continuous basis. A set of indicator thresholds is defined. Each indicator threshold corresponds to a quantifiable physiological measure of a pathophysiology indicative of congestive heart failure and relates to the same type of patient information as at least one of the recorded measures. A congestive heart failure finding is diagnosed. A change in patient status is determined by comparing at least one recorded measure to at least one other recorded measure with both recorded measures relating to the same type of patient information. Each patient status change is compared to the indicator threshold corresponding to the same type of patient information as the recorded measures that were compared.

A further embodiment is an automated patient care system and method for diagnosing and monitoring congestive heart failure and outcomes thereof. Recorded measures organized into a monitoring set for an individual patient are stored into a database. Each recorded measure is recorded on a substantially continuous basis and relates to at least one aspect of monitoring reduced exercise capacity and/or respiratory distress. A plurality of the monitoring sets is periodically retrieved from the database. At least one measure related to congestive heart failure onset, progression, regression, and status quo is evaluated. A patient status change is determined by comparing at least one recorded measure from each of the monitoring sets to at least one other recorded measure with both recorded measures relating to the same type of patient information. Each patient status change is tested against an indicator threshold corresponding to the same type of patient information as the recorded measures that were compared. The indicator threshold corresponds to a quantifiable physiological measure of a pathophysiology indicative of reduced exercise capacity and/or respiratory distress.

The present invention provides a capability to detect and track subtle trends and incremental changes in recorded patient information for diagnosing and monitoring congestive heart failure. When coupled with an enrollment in a remote patient monitoring service having the capability to remotely and continuously collect and analyze external or implantable medical device measures, congestive heart failure detection, prevention, and tracking regression from therapeutic maneuvers become feasible.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 6 is a record view showing, by way of example, a set of partial patient care records for care of patients with congestive heart failure stored in the database of the system of FIG. 1;

DETAILED DESCRIPTION

Figure 1:
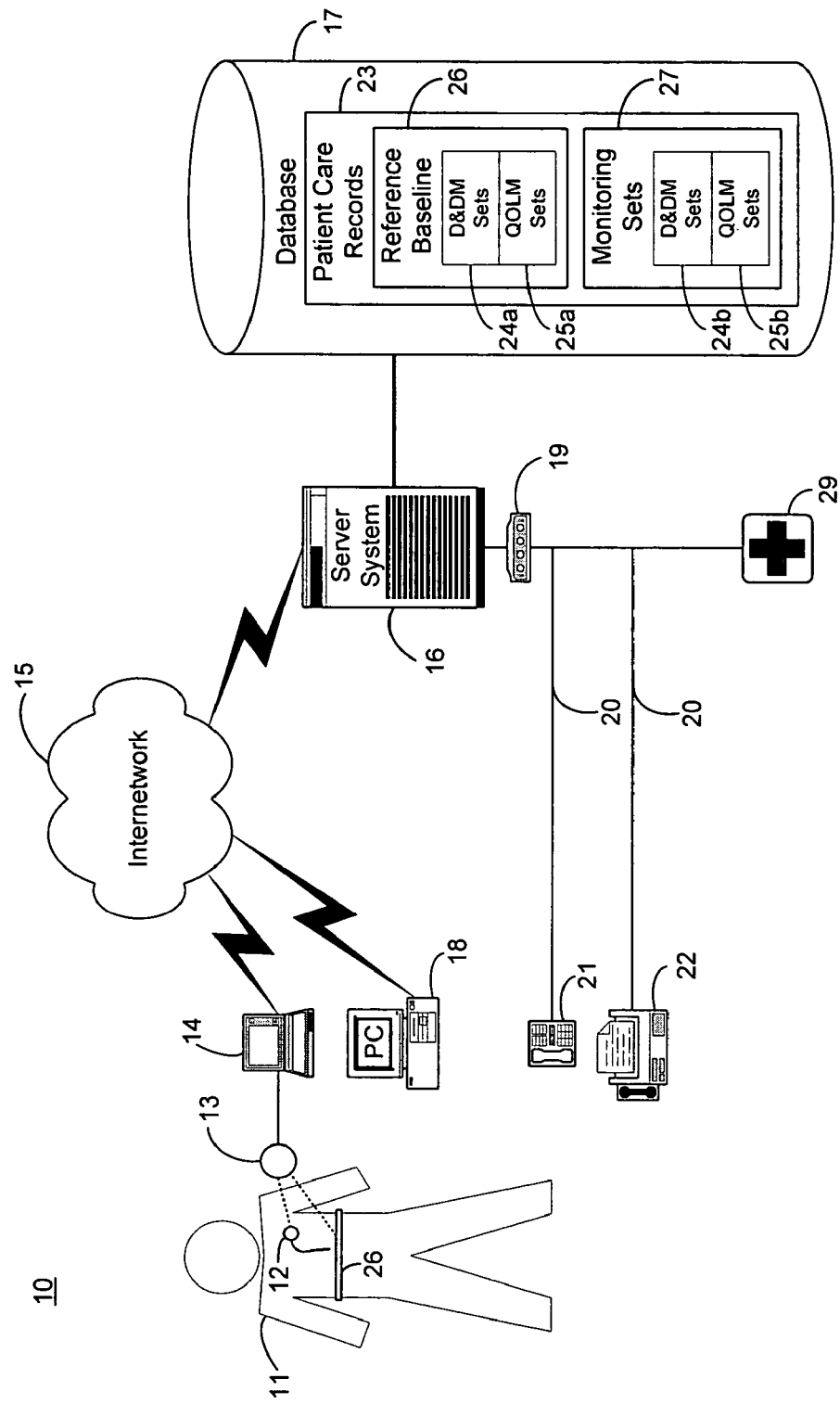
FIG. 1 is a block diagram showing an automated collection and analysis patient care system for providing diagnosis and monitoring of congestive heart failure in accordance with the present invention.

FIG. 1 is a block diagram showing an automated collection and analysis patient care system 10 for providing diagnosis and monitoring of congestive heart failure in accordance with the present invention. An exemplary automated collection and analysis patient care system suitable for use with the present invention is disclosed in the related, commonly-owned U.S. Pat. No. 6,312,378, issued Nov. 6, 2001, the disclosure of which is incorporated herein by reference. Preferably, an individual patient 11 is a recipient of an implantable medical device 12, such as, by way of example, an IPG, cardiovascular or heart failure monitor, or therapeutic device, with a set of leads extending into his or her heart and electrodes implanted throughout the cardiopulmonary system. Alternatively, an external monitoring or therapeutic medical device 26, a subcutaneous monitor or device inserted into other organs, a cutaneous monitor, or even a manual physiological measurement device, such as an electrocardiogram or heart rate monitor, could be used. The implantable medical device 12 and external medical device 26 include circuitry for recording into a short-term, volatile memory telemetered signals stored for later retrieval, which become part of a set of device and derived measures, such as described below, by way of example, with reference to FIG. 2. Exemplary implantable medical devices suitable for use in the present invention include the Discovery line of pacemakers, manufactured by Guidant Corporation, Indianapolis, Ind., and the Gem line of ICDs, manufactured by Medtronic Corporation, Minneapolis, Minn.

The telemetered signals stored in the implantable medical device 12 are preferably retrieved upon the completion of an initial observation period and subsequently thereafter on a continuous, periodic (daily) basis, such as described in the related, commonly-owned U.S. Pat. No. 6,221,011, issued Apr. 24, 2001, the disclosure of which is incorporated herein by reference. A programmer 14, personal computer 18, or similar device for communicating with an implantable medical device 12 can be used to retrieve the telemetered signals. A magnetized reed switch (not shown) within the implantable medical device 12 closes in response to the placement of a wand 13 over the site of the implantable medical device 12. The programmer 14 sends programming or interrogating instructions to and retrieves stored telemetered signals from the implantable medical device 12 via RF signals exchanged through the wand 13. Similar communication means are used for accessing the external medical device 26. Once downloaded, the telemetered signals are sent via an internetwork 15, such as the Internet, to a server system 16 which periodically receives and stores the telemetered signals as device measures in patient care records 23 in a database 17, as further described below, by way of example, with reference to FIGS. 2 and 3. An exemplary programmer 14 suitable for use in the present invention is the Model 2901 Programmer Recorder Monitor, manufactured by Guidant Corporation, Indianapolis, Ind.

The patient 11 is remotely monitored by the server system 16 via the internetwork 15 through the periodic receipt of the retrieved device measures from the implantable medical device 12 or external medical device 26. The patient care records 23 in the database 17 are organized into two identified sets of device measures: an optional reference baseline 26 recorded during an initial observation period and monitoring sets 27 recorded subsequently thereafter. The device measures sets are periodically analyzed and compared by the server system 16 to indicator thresholds corresponding to quantifiable physiological measures of a pathophysiology indicative of congestive heart failure, as further described below with reference to FIG. 5. As necessary, feedback is provided to the patient 11. By way of example, the feedback includes an electronic mail message automatically sent by the server system 16 over the internetwork 15 to a personal computer 18 (PC) situated for local access by the patient 11. Alternatively, the feedback can be sent through a telephone interface device 19 as an automated voice mail message to a telephone 21 or as an automated facsimile message to a facsimile machine 22, both also situated for local access by the patient 11. Moreover, simultaneous notifications can also be delivered to the patient's physician, hospital, or emergency medical services provider 29 using similar feedback means to deliver the information.

The server system 10 can consist of either a single computer system or a cooperatively networked or clustered set of computer systems. Each computer system is a general purpose, programmed digital computing device consisting of a central processing unit (CPU), random access memory (RAM), non-volatile secondary storage, such as a hard drive or CD ROM drive, network interfaces, and peripheral devices, including user interfacing means, such as a keyboard and display. Program code, including software programs, and data are loaded into the RAM for execution and processing by the CPU and results are generated for display, output, transmittal, or storage, as is known in the art.

Figure 2:
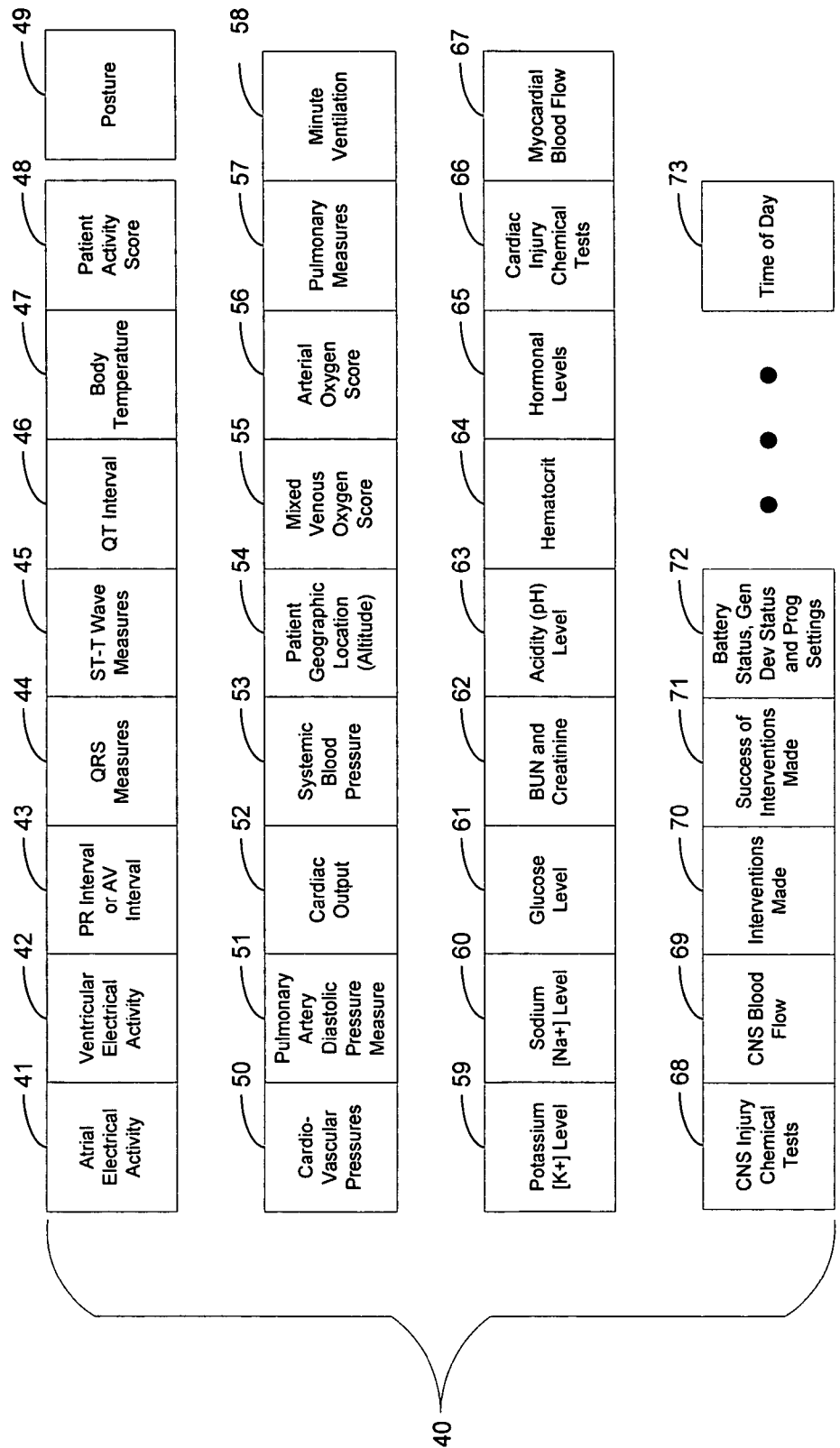
FIG. 2 is a database schema showing, by way of example, the organization of a device and derived measures set record for care of patients with congestive heart failure stored as part of a patient care record in the database of the system of FIG. 1.

The database 17 stores patient care records 23 for each individual patient to whom remote patient care is being provided. Each patient care record 23 contains normal patient identification and treatment profile information, as well as medical history, medications taken, height and weight, and other pertinent data (not shown). The patient care records 23 consist primarily of two sets of data: device and derived measures (D&DM) sets 24a, 24b and quality of life (QOL)

sets 25a, 25b, the organization of which are further described below with respect to FIGS. 2 and 3, respectively. The device and derived measures sets 24a, 24b and quality of life and symptom measures sets 25a, 25b can be further logically categorized into two potentially overlapping sets. The reference baseline 26 is a special set of device and derived reference measures sets 24a and quality of life and symptom measures sets 25a recorded and determined during an initial observation period. Monitoring sets 27 are device and derived measures sets 24b and quality of life and symptom measures sets 25b recorded and determined thereafter on a regular, continuous basis. Other forms of database organization are feasible.

The implantable medical device 12 and, in a more limited fashion, the external medical device 26, record patient information for care of patients with congestive heart failure on a regular basis. The recorded patient information is downloaded and stored in the database 17 as part of a patient care record 23. Further patient information can be derived from recorded data, as is known in the art. FIG. 2 is a database schema showing, by way of example, the organization of a device and derived measures set record 40 for patient care stored as part of a patient care record in the database 17 of the system of FIG. 1. Each record 40 stores patient information which includes a snapshot of telemetered signals data which were recorded by the implantable medical device 12 or the external medical device 26, for instance, on per heartbeat, binned average or derived bases; measures derived from the recorded device measures; and manually collected information, such as obtained through a patient medical history interview or questionnaire. The following non-exclusive information can be recorded for a patient: atrial electrical activity 41, ventricular electrical activity 42, PR interval or AV interval 43, QRS measures 44, ST-T wave measures 45, QT interval 46, body temperature 47, patient activity score 48, posture 49, cardiovascular pressures 50, pulmonary artery diastolic pressure measure 51, cardiac output 52, systemic blood pressure 53, patient geographic location (altitude) 54, mixed venous oxygen score 55, arterial oxygen score 56, pulmonary measures 57, minute ventilation 58, potassium [K+] level 59, sodium [Na+] level 60, glucose level 61, blood urea nitrogen (BUN) and creatinine 62, acidity (pH) level 63, hematocrit 64, hormonal levels 65, cardiac injury chemical tests 66, myocardial blood flow 67, central nervous system (CNS) injury chemical tests 68, central nervous system blood flow 69, interventions made by the implantable medical device or external medical device 70, and the relative success of any interventions made 71. In addition, the implantable medical device or external medical device communicates device-specific information, including battery status, general device status and program settings 72 and the time of day 73 for the various recorded measures. Other types of collected, recorded, combined, or derived measures are possible, as is known in the art.

Figure 3:
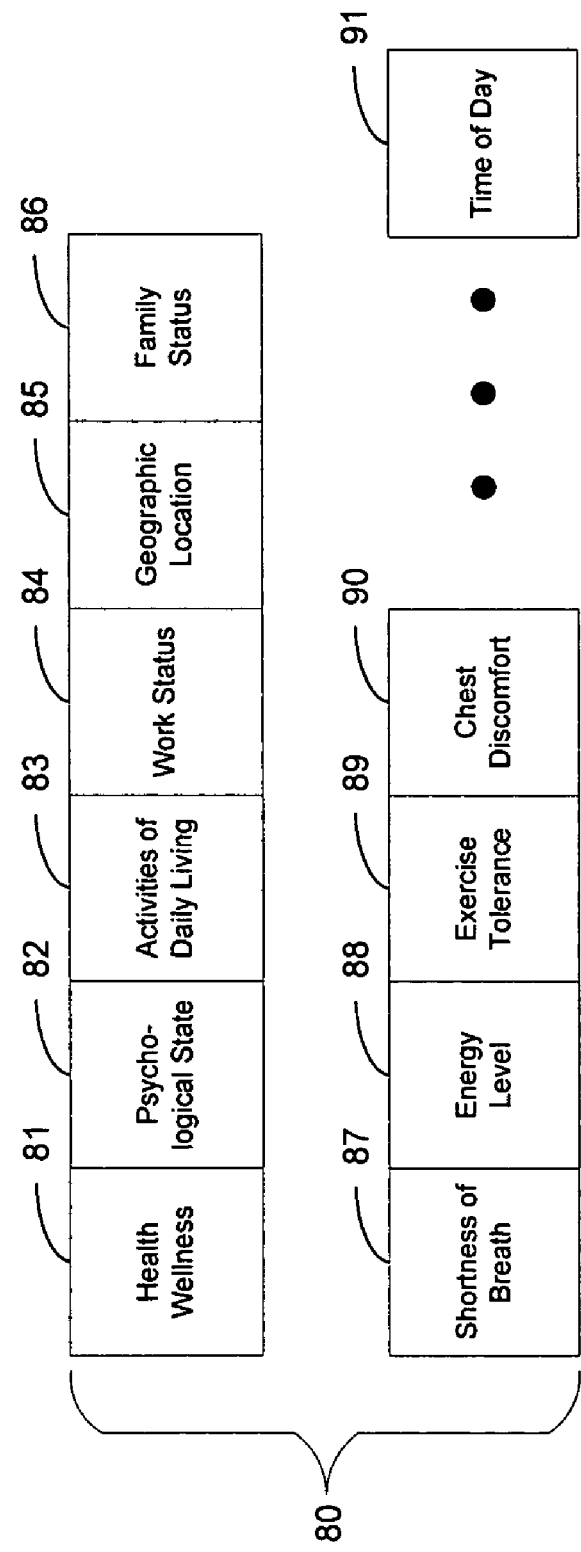
FIG. 3 is a database schema showing, by way of example, the organization of a quality of life and symptom measures set record for care of patients with congestive heart failure stored as part of a patient care record in the database of the system of FIG. 1.

The device and derived measures sets 24a, 24b (shown in FIG. 1), along with quality of life and symptom measures sets 25a, 25b, as further described below with reference to FIG. 3, are continuously and periodically received by the server system 16 as part of the on-going patient care monitoring and analysis function. These regularly collected data sets are collectively categorized as the monitoring sets 27 (shown in FIG. 1). In addition, select device and derived measures sets 24a and quality of life and symptom measures sets 25a can be designated as a reference baseline 26 at the outset of patient care to improve the accuracy and meaningfulness of the serial monitoring sets 27. Select patient information is collected, recorded, and derived during an initial period of observation or patient care, such as described in the related, commonly-owned U.S. Pat. No. 6,221,011, issued Apr. 24, 2001, the disclosure of which is incorporated herein by reference.

As an adjunct to remote patient care through the monitoring of measured physiological data via the implantable medical device 12 or external medical device 26, quality of life and symptom measures sets 25a can also be stored in the database 17 as part of the reference baseline 26, if used, and the monitoring sets 27. A quality of life measure is a semi-quantitative self-assessment of an individual patient's physical and emotional well-being and a record of symptoms, such as provided by the Duke Activities Status Indicator. These scoring systems can be provided for use by the patient 11 on the personal computer 18 (shown in FIG. 1) to record his or her quality of life scores for both initial and periodic download to the server system 16. FIG. 3 is a database schema showing, by way of example, the organization of a quality of life record 80 for use in the database 17. The following information is recorded for a patient: overall health wellness 81, psychological state 82, activities of daily living 83, work status 84, geographic location 85, family status 86, shortness of breath 87, energy level 88, exercise tolerance 89, chest discomfort 90, time of day 91, and other quality of life and symptom measures as would be known to one skilled in the art.

Other types of quality of life and symptom measures are possible, such as those indicated by responses to the Minnesota Living with Heart Failure Questionnaire described in E. Braunwald, ed., "Heart Disease—A Textbook of Cardiovascular Medicine," pp. 452-454, W. B. Saunders Co. (1997), the disclosure of which is incorporated herein by reference. Similarly, functional classifications based on the relationship between symptoms and the amount of effort required to provoke them can serve as quality of life and symptom measures, such as the New York Heart Association (NYHA) classifications I, II, III and IV, also described in Ibid.

The patient may also add non-device quantitative measures, such as the six-minute walk distance, as complementary data to the device and derived measures sets 24a, 24b and the symptoms during the six-minute walk to quality of life and symptom measures sets 25a, 25b.

Figure 4:
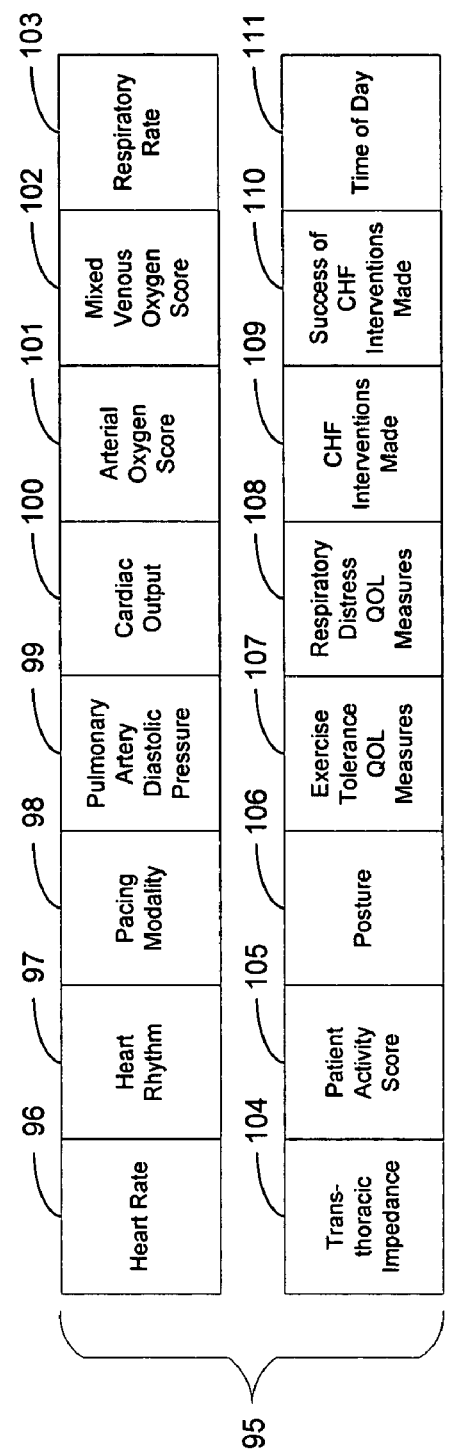
FIG. 4 is a database schema showing, by way of example, the organization of a combined measures set record for care of patients with congestive heart failure stored as part of a patient care record in the database of the system of FIG. 1.

On a periodic basis, the patient information stored in the database 17 is analyzed and compared to pre-determined cutoff levels, which, when exceeded, can provide etiological indications of congestive heart failure symptoms. FIG. 4 is a database schema showing, by way of example, the organization of a combined measures set record 95 for use in the database 17. Each record 95 stores patient information obtained or derived from the device and derived measures sets 24a, 24b and quality of life and symptom measures sets 25a, 25b as maintained in the reference baseline 26, if used, and the monitoring sets 27. The combined measures set 95 represents those measures most (but not exhaustively or exclusively) relevant to a pathophysiology indicative of congestive heart failure and are determined as further described below with reference to FIGS. 8A-8B. The following information is stored for a patient: heart rate 96, heart rhythm (e.g., normal sinus vs. atrial fibrillation) 97, pacing modality 98, pulmonary artery diastolic pressure 99, cardiac output 100, arterial oxygen score 101, mixed venous oxygen score 102, respiratory rate 103, transthoracic impedance 104, patient activity score 105, posture 106, exercise tolerance quality of life and symptom measures 107, respiratory distress quality of life and symptom measures 108, any interventions made to treat congestive heart failure 109, including treatment by medical device, via drug infusion administered by the patient or by a medical device, surgery, and any other form of medical intervention as is known in the art, the relative success of any such interventions made 110, and time of day 111. Other types of comparison measures regarding congestive heart failure are possible as is known in the art. In the described embodiment, each combined measures set 95 is sequentially retrieved from the database 17 and processed. Alternatively, each combined measures set 95 could be stored within a dynamic data structure maintained transitorily in the random access memory of the server system 16 during the analysis and comparison operations.

Figure 5:
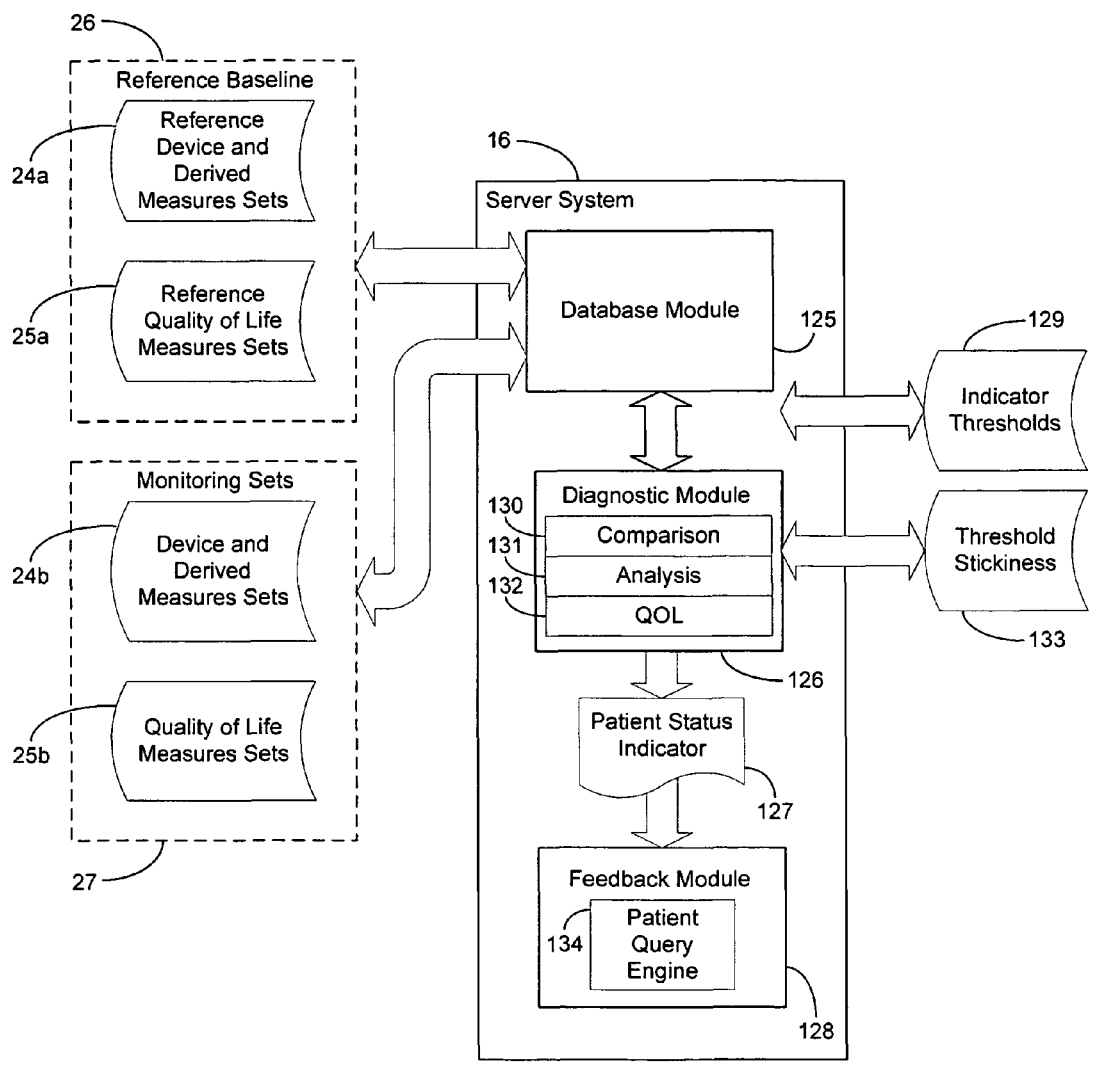
FIG. 5 is a block diagram showing the software modules of the server system of the system of FIG. 1.

FIG. 5 is a block diagram showing the software modules of the server system 16 of the system 10 of FIG. 1. Each module is a computer program written as source code in a conventional programming language, such as the C or Java programming languages, and is presented for execution by the CPU of the server system 16 as object or byte code, as is known in the art. The various implementations of the source code and object and byte codes can be held on a computer-readable storage medium or embodied on a transmission medium in a carrier wave. The server system 16 includes three primary software modules, database module 125, diagnostic module 126, and feedback module 128, which perform integrated functions as follows.

First, the database module 125 organizes the individual patient care records 23 stored in the database 17 (shown in FIG. 1) and efficiently stores and accesses the reference baseline 26, monitoring sets 27, and patient care data maintained in those records. Any type of database organization could be utilized, including a flat file system, hierarchical database, relational database, or distributed database, such as provided by database vendors, such as Oracle Corporation, Redwood Shores, Calif.

Next, the diagnostic module 126 makes findings of congestive heart failure based on the comparison and analysis of the data measures from the reference baseline 26 and monitoring sets 27. The diagnostic module includes three modules: comparison module 130, analysis module 131, and quality of life module 132. The comparison module 130 compares recorded and derived measures retrieved from the reference baseline 26, if used, and monitoring sets 27 to indicator thresholds 129. The database 17 stores individual patient care records 23 for patients suffering from various health disorders and diseases for which they are receiving remote patient care. For purposes of comparison and analysis by the comparison module 130, these records can be categorized into peer groups containing the records for those patients suffering from similar disorders, as well as being viewed in reference to the overall patient population. The definition of the peer group can be progressively refined as the overall patient population grows. To illustrate, FIG. 6 is a record view showing, by way of example, a set of partial patient care records for care of patients with congestive heart failure stored in the database 17 for three patients, Patient 1, Patient 2, and Patient 3. For each patient, three sets of peer measures, X, Y, and Z, are shown. Each of the measures, X, Y, and Z, could be either collected or derived measures from the reference baseline 26, if used, and monitoring sets 27.

The same measures are organized into time-based sets with Set 0 representing sibling measures made at a reference time t=0. Similarly, Set n−2, Set n−1 and Set n each represent sibling measures made at later reference times t=n−2, t=n−1 and t=n, respectively. Thus, for a given patient, such as Patient 1, serial peer measures, such as peer measure $X_0$ through $X_n$, represent the same type of patient information monitored over time. The combined peer measures for all patients can be categorized into a health disorder- or disease-matched peer group. The definition of disease-matched peer group is a progressive definition, refined over time as the number of monitored patients grows. Measures representing different types of patient information, such as measures $X_0$, $Y_0$, and $Z_0$, are sibling measures. These are measures which are also measured over time, but which might have medically significant meaning when compared to each other within a set for an individual patient.

The comparison module 130 performs two basic forms of comparison. First, individual measures for a given patient can be compared to other individual measures for that same patient (self-referencing). These comparisons might be peer-to-peer measures, that is, measures relating to a one specific type of patient information, projected over time, for instance, $X_n, X_{n-1}, X_{n-2}, \ldots X_0$, or sibling-to-sibling measures, that is, measures relating to multiple types of patient information measured during the same time period, for a single snapshot, for instance, $X_n$, $Y_n$, and $Z_n$, or projected over time, for instance, $X_n, Y_n, Z_n, X_{n-1}, Y_{n-1}, Z_{n-1}, X_{n-2}, Y_{n-2}, Z_{n-2}, \ldots X_0, Y_0, Z_0$. Second, individual measures for a given patient can be compared to other individual measures for a group of other patients sharing the same disorder- or disease-specific characteristics (peer group referencing) or to the patient population in general (population referencing). Again, these comparisons might be peer-to-peer measures projected over time, for instance, $X_n, X_{n'}, X_{n''}, X_{n-1}, X_{n-1'}, X_{n-1''}, X_{n-2}, X_{n-2'}, X_{n-2''} \ldots X_0, X_{0'}, X_{0''}$, or comparing the individual patient's measures to an average from the group. Similarly, these comparisons might be sibling-to-sibling measures for single snapshots, for instance, $X_n, X_{n'}, X_{n''}, Y_n, Y_{n'}, Y_{n''}$, and $Z_n, Z_{n'}, Z_{n''}$, or projected over time, for instance, $X_n, X_{n'}, X_{n''}, Y_n, Y_{n'}, Y_{n''}, Z_n, Z_{n'}, Z_{n''}, X_{n-1}, X_{n-1'}, X_{n-1''}, Y_{n-1}, Y_{n-1'}, Y_{n-1''}, Z_{n-1}, Z_{n-1'}, Z_{n-1''}, X_{n-2}, X_{n-2'}, X_{n-2''}, Y_{n-2}, Y_{n-2'}, Y_{n-2''}, Z_{n-2}, Z_{n-2'}, Z_{n-2''} \ldots X_0, X_{0'}, X_{0''}, Y_0, Y_{0'}, Y_{0''}$, and $Z_0, Z_{0'}, Z_{0''}$. Other forms of comparisons are feasible, including multiple disease diagnoses for diseases exhibiting similar abnormalities in physiological measures that might result from a second disease but manifest in different combinations or onset in different temporal sequences.

Figure 7:
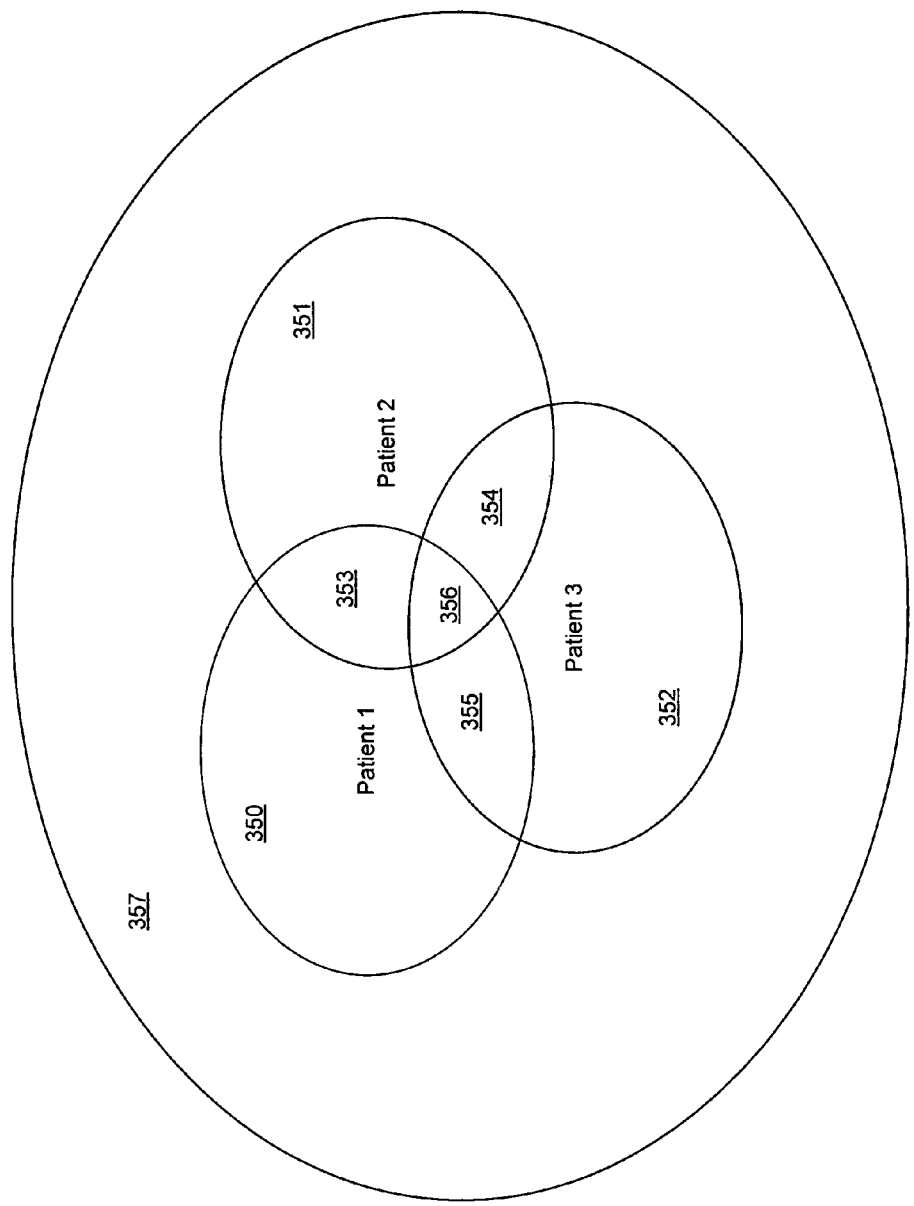
FIG. 7 is a Venn diagram showing, by way of example, peer group overlap between the partial patient care records of FIG. 6.

FIG. 7 is a Venn diagram showing, by way of example, peer group overlap between the partial patient care records 23 of FIG. 1. Each patient care record 23 includes characteristics data 350, 351, 352, including personal traits, demographics, medical history, and related personal data, for patients 1, 2 and 3, respectively. For example, the characteristics data 350 for patient 1 might include personal traits which include gender and age, such as male and an age between 40-45; a demographic of resident of New York City; and a medical history consisting of anterior myocardial infraction, congestive heart failure and diabetes. Similarly, the characteristics data 351 for patient 2 might include identical personal traits, thereby resulting in partial overlap 353 of characteristics data 350 and 351. Similar characteristics overlap 354, 355, 356 can exist between each respective patient. The overall patient population 357 would include the universe of all characteristics data. As the monitoring population grows, the number of patients with personal traits matching those of the monitored patient will grow, increasing the value of peer group referencing. Large peer groups, well matched across all monitored measures, will result in a well known natural history of disease and will allow for more accurate prediction of the clinical course of the patient being monitored. If the population of patients is relatively small, only some traits 356 will be uniformly present in any particular peer group. Eventually, peer groups, for instance, composed of 100 or more patients each, would evolve under conditions in which there would be complete overlap of substantially all salient data, thereby forming a powerful core reference group for any new patient being monitored.

Referring back to FIG. 5, the analysis module 131 analyzes the results from the comparison module 130, which are stored as a combined measures set 95 (not shown), to a set of indicator thresholds 129, as further described below with reference to FIGS. 8A-8B. Similarly, the quality of life module 132 compares quality of life and symptom measures set 25a, 25b from the reference baseline 26 and monitoring sets 27, the results of which are incorporated into the comparisons performed by the analysis module 131, in part, to either refute or support the findings based on physiological "hard" data. Finally, the feedback module 128 provides automated feedback to the individual patient based, in part, on the patient status indicator 127 generated by the diagnostic module 126. As described above, the feedback could be by electronic mail or by automated voice mail or facsimile. The feedback can also include normalized voice feedback, such as described in the related, commonly-owned U.S. Pat. No. 6,203,495, issued Mar. 20, 2001, the disclosure of which is incorporated herein by reference. In one embodiment, a remote client processes voice feedback into a set of quality of life measures which each relate to patient self-assessment indicators, the voice feedback having been spoken by the individual patient substantially contemporaneous to the collection of an identifiable device measures set. In addition, the feedback module 128 determines whether any changes to interventive measures are appropriate based on threshold stickiness ("hysteresis") 133, as further described below with reference to FIG. 16. The threshold stickiness 133 can prevent fickleness in diagnostic routines resulting from transient, non-trending and non-significant fluctuations in the various collected and derived measures in favor of more certainty in diagnosis. In a further embodiment of the present invention, the feedback module 128 includes a patient query engine 134 which enables the individual patient 11 to interactively query the server system 16 regarding the diagnosis, therapeutic maneuvers, and treatment regimen. Conversely, the patient query engines 134, found in interactive expert systems for diagnosing medical conditions, can interactively query the patient. Using the personal computer 18 (shown in FIG. 1), the patient can have an interactive dialogue with the automated server system 16, as well as human experts as necessary, to self assess his or her medical condition. Such expert systems are well known in the art, an example of which is the MYCIN expert system developed at Stanford University and described in Buchanan, B. & Shortlife, E., "RULE-BASED EXPERT SYSTEMS. The MYCIN Experiments of the Stanford Heuristic Programming Project," Addison-Wesley (1984). The various forms of feedback described above help to increase the accuracy and specificity of the reporting of the quality of life and symptomatic measures.

Figure 8A:
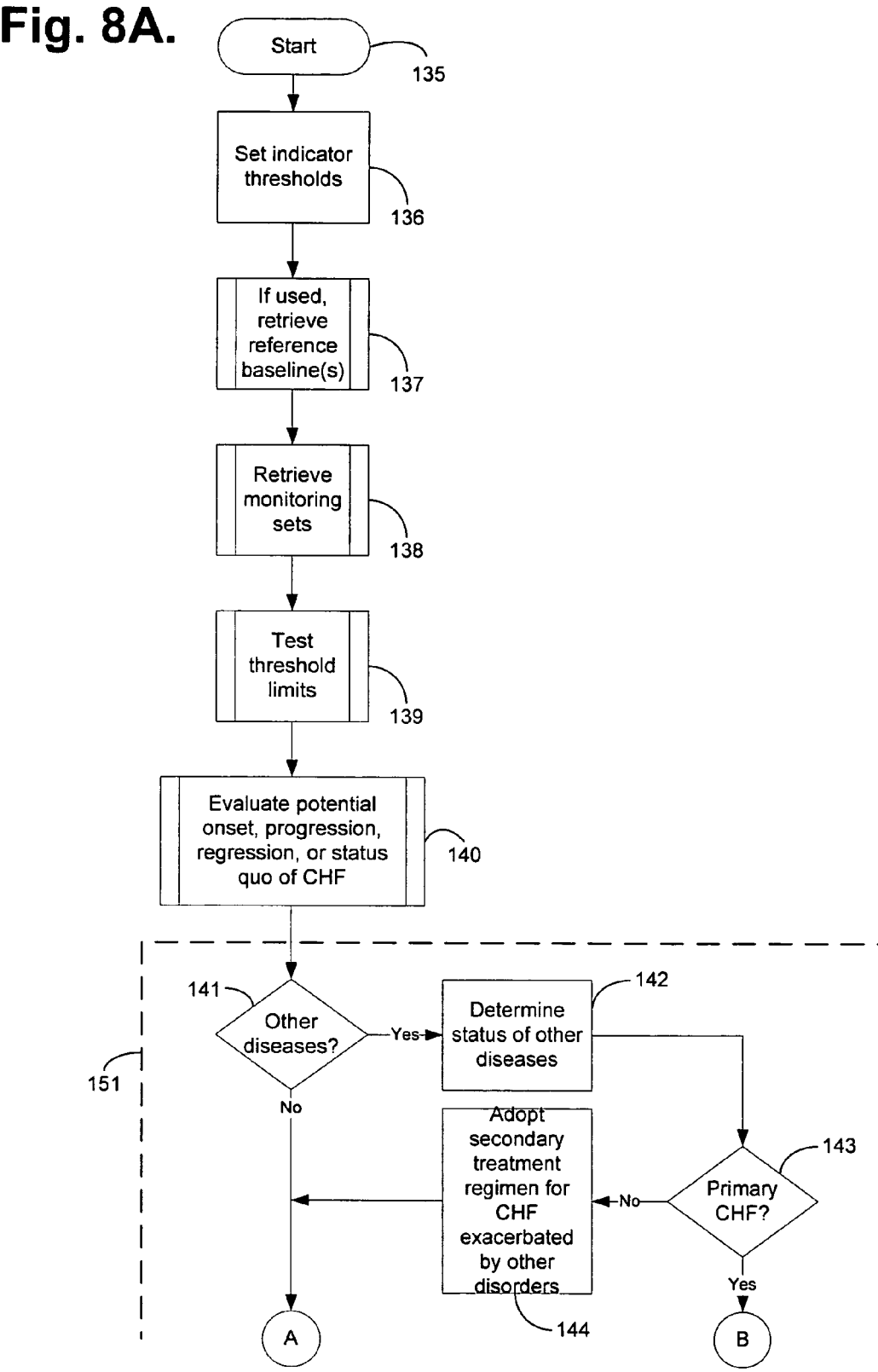
FIGS. 8A-8B are flow diagrams showing a method for providing diagnosis and monitoring of congestive heart failure for use in automated patient care in accordance with the present invention.
Figure 8B:
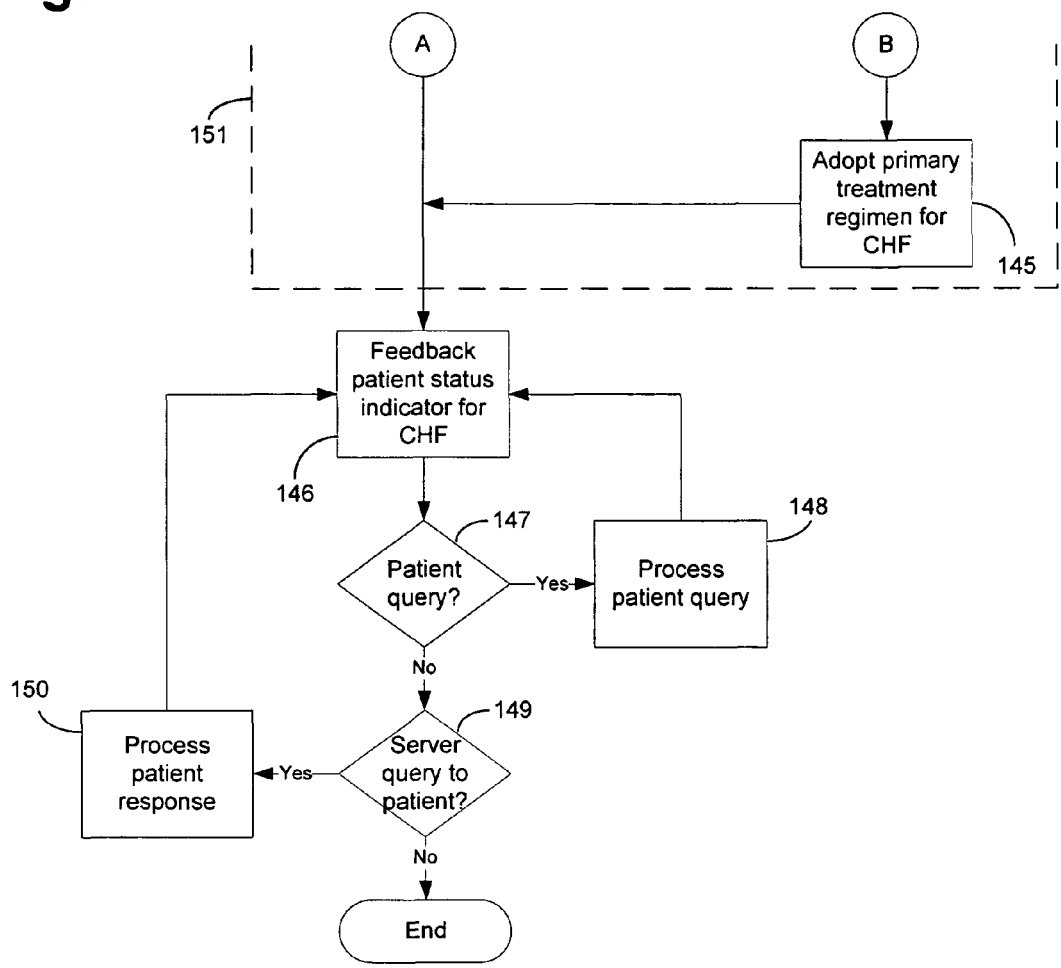

FIGS. 8A-8B are flow diagrams showing a method for providing diagnosis and monitoring of congestive heart failure for use in automated patient care 135 in accordance with the present invention. First, the indicator thresholds 129 (shown in FIG. 5) are set (block 136) by defining a quantifiable physiological measure of a pathophysiology indicative of congestive heart failure and relating to the each type of patient information in the combined device and derived measures set 95 (shown in FIG. 4). The actual values of each indicator threshold can be finite cutoff values, weighted values, or statistical ranges, as discussed below with reference to FIGS. 11A-11D. Next, the reference baseline 26 (block 137) and monitoring sets 27 (block 138) are retrieved from the database 17, as further described below with reference to FIGS. 9 and 10, respectively. Each measure in the combined device and derived measures set 95 is tested against the threshold limits defined for each indicator threshold 129 (block 139), as further described below with reference to FIGS. 11A-11D. The potential onset, progression, regression, or status quo of congestive heart failure is then evaluated (block 140) based upon the findings of the threshold limits tests (block 139), as further described below with reference to FIGS. 13A-13B, 14A-14B, 15A-15B.

In a further embodiment, multiple near-simultaneous disorders are considered in addition to primary congestive heart failure. Primary congestive heart failure is defined as the onset or progression of congestive heart failure without obvious inciting cause. Secondary congestive heart failure is defined as the onset or progression of congestive heart failure (in a patient with or without pre-existing congestive heart failure) from another disease process, such as coronary insufficiency, respiratory insufficiency, atrial fibrillation, and so forth. Other health disorders and diseases can potentially share the same forms of symptomatology as congestive heart failure, such as myocardial ischemia, respiratory insufficiency, pneumonia, exacerbation of chronic bronchitis, renal failure, sleep-apnea, stroke, anemia, atrial fibrillation, other cardiac arrhythmias, and so forth. If more than one abnormality is present, the relative sequence and magnitude of onset of abnormalities in the monitored measures becomes most important in sorting and prioritizing disease diagnosis and treatment.

Thus, if other disorders or diseases are being cross-referenced and diagnosed (block 141), their status is determined (block 142). In the described embodiment, the operations of ordering and prioritizing multiple near-simultaneous disorders (box 151) by the testing of threshold limits and analysis in a manner similar to congestive heart failure as described above, preferably in parallel to the present determination, is described in the related, commonly-owned U.S. Pat. No. 6,440,066, issued Aug. 27, 2002, the disclosure of which is incorporated herein by reference. If congestive heart failure is due to an obvious inciting cause, i.e., secondary congestive heart failure, (block 143), an appropriate treatment regimen for congestive heart failure as exacerbated by other disorders is adopted that includes treatment of secondary disorders, e.g., myocardial ischemia, respiratory insufficiency, atrial fibrillation, and so forth (block 144) and a suitable patient status indicator 127 for congestive heart failure is provided (block 146) to the patient. Suitable devices and approaches to diagnosing and treating myocardial infarction, respiratory distress and atrial fibrillation are described in related, commonly-owned U.S. Pat. No. 6,368,284, issued Apr. 9, 2002; 6,398,728, issued Jun. 4, 2002; and U.S. Pat. No. 6,411,840, issued Jun. 25, 2002, the disclosures of which are incorporated herein by reference.

Otherwise, if primary congestive heart failure is indicated (block 143), a primary treatment regimen is followed (block 145). A patient status indicator 127 for congestive heart failure is provided (block 146) to the patient regarding physical well-being, disease prognosis, including any determinations of disease onset, progression, regression, or status quo, and other pertinent medical and general information of potential interest to the patient.

Finally, in a further embodiment, if the patient submits a query to the server system 16 (block 147), the patient query is interactively processed by the patient query engine (block 148). Similarly, if the server elects to query the patient (block 149), the server query is interactively processed by the server query engine (block 150). The method then terminates if no further patient or server queries are submitted.

Figure 9:
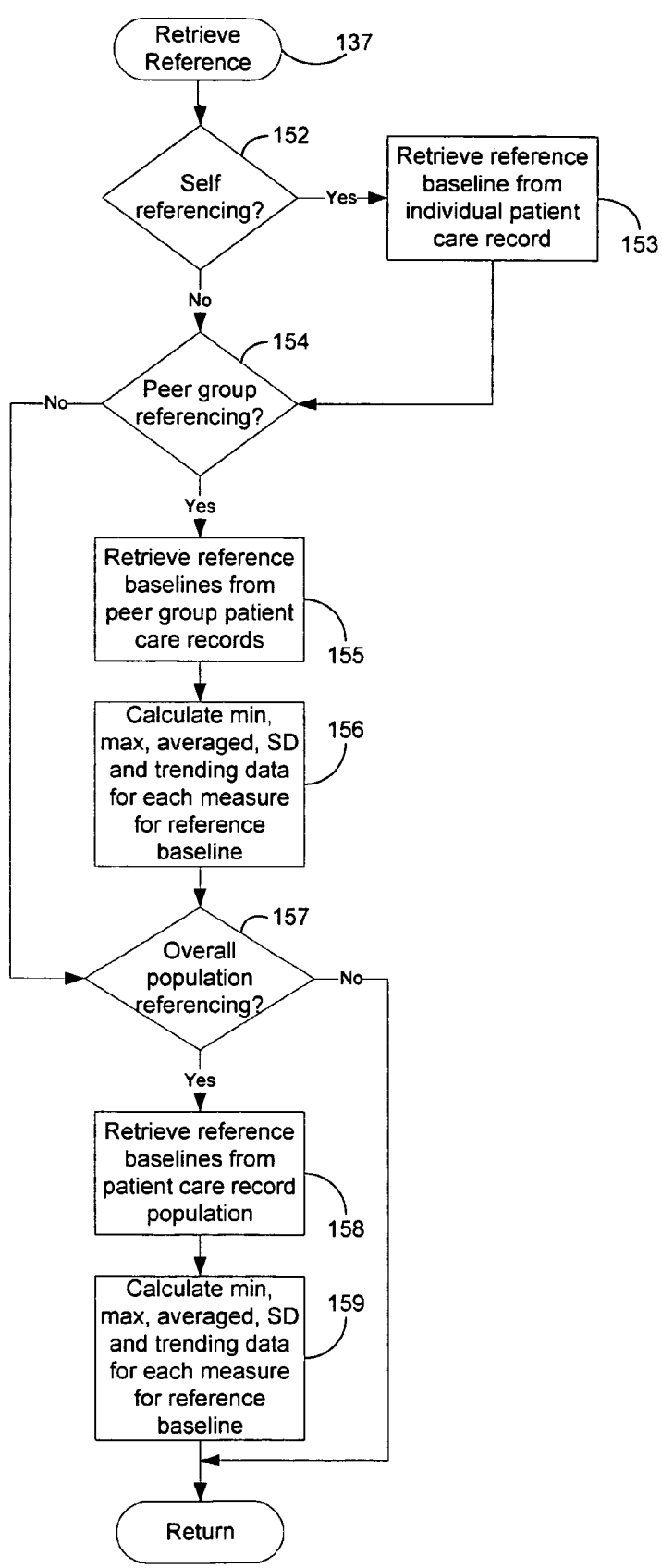
FIG. 9 is a flow diagram showing the routine for retrieving reference baseline sets for use in the method of FIGS. 8A-8B.

FIG. 9 is a flow diagram showing the routine for retrieving reference baseline sets 137 for use in the method of FIGS. 8A-8B. The purpose of this routine is to retrieve the appropriate reference baseline sets 26, if used, from the database 17 based on the types of comparisons being performed. First, if the comparisons are self referencing with respect to the measures stored in the individual patient care record 23 (block 152), the reference device and derived measures set 24a and reference quality of life and symptom measures set 25a, if used, are retrieved for the individual patient from the database 17 (block 153). Next, if the comparisons are peer group referencing with respect to measures stored in the patient care records 23 for a health disorder- or disease-specific peer group (block 154), the reference device and derived measures set 24a and reference quality of life and symptom measures set 25a, if used, are retrieved from each patient care record 23 for the peer group from the database 17 (block 155). Data for each measure (e.g., minimum, maximum, averaged, standard deviation (SD), and trending data) from the reference baseline 26 for the peer group is then calculated (block 156). Finally, if the comparisons are population referencing with respect to measures stored in the patient care records 23 for the overall patient population (block 157), the reference device and derived measures set 24a and reference quality of life and symptom measures set 25a, if used, are retrieved from each patient care record 23 from the database 17 (block 158). Minimum, maximum, averaged, standard deviation, and trending data and other numerical processes using the data, as is known in the art, for each measure from the reference baseline 26 for the peer group is then calculated (block 159). The routine then returns.

Figure 10:
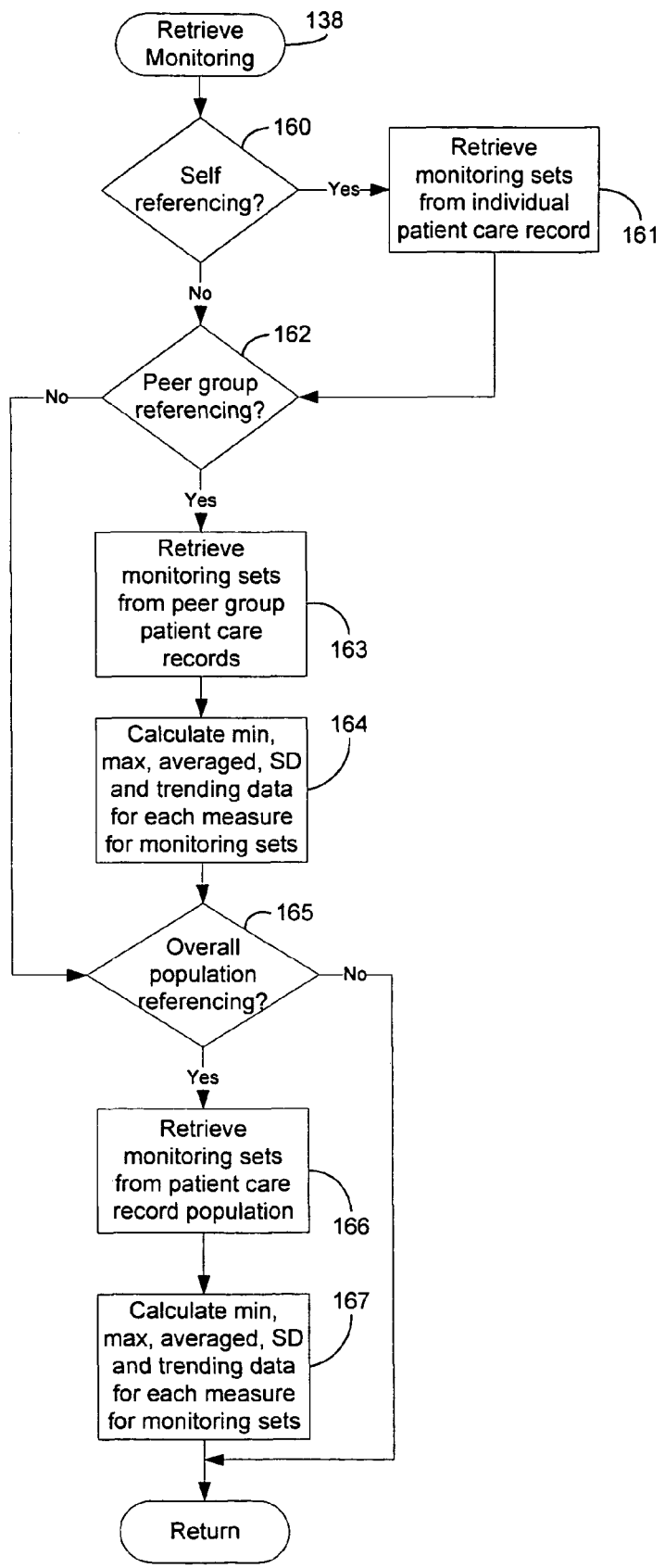
FIG. 10 is a flow diagram showing the routine for retrieving monitoring sets for use in the method of FIGS. 8A-8B.
Figure 11A:
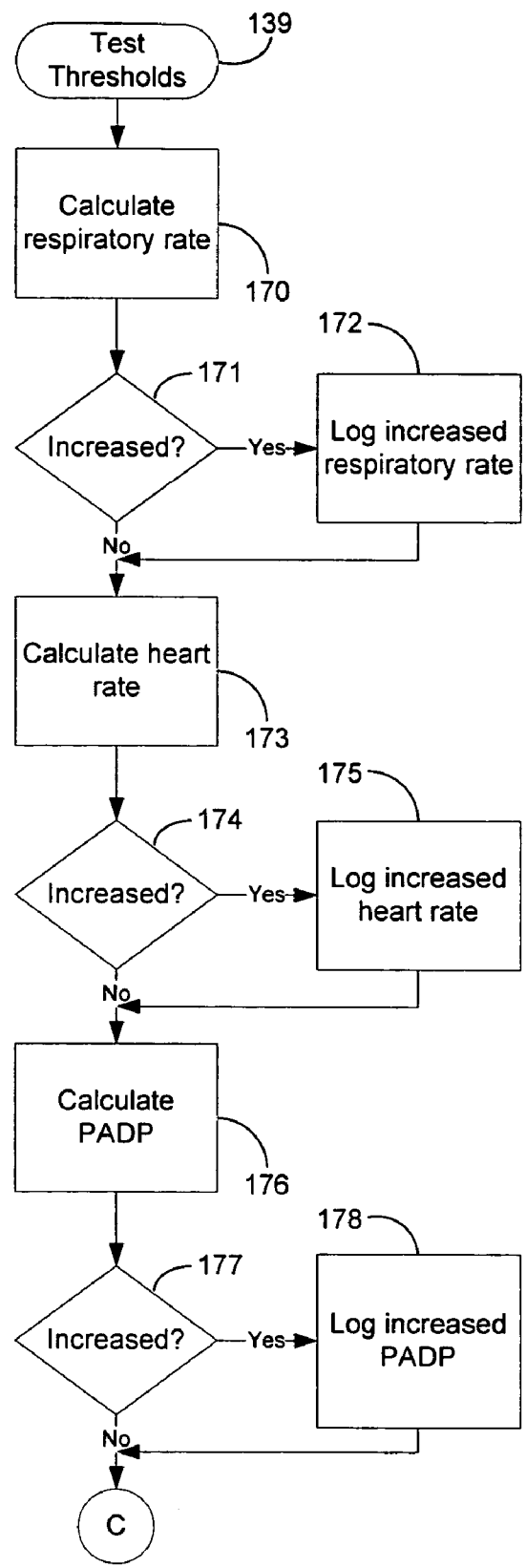
FIGS. 11A-11D are flow diagrams showing the routine for testing threshold limits for use in the method of FIGS. 8A-8B.
Figure 11B:
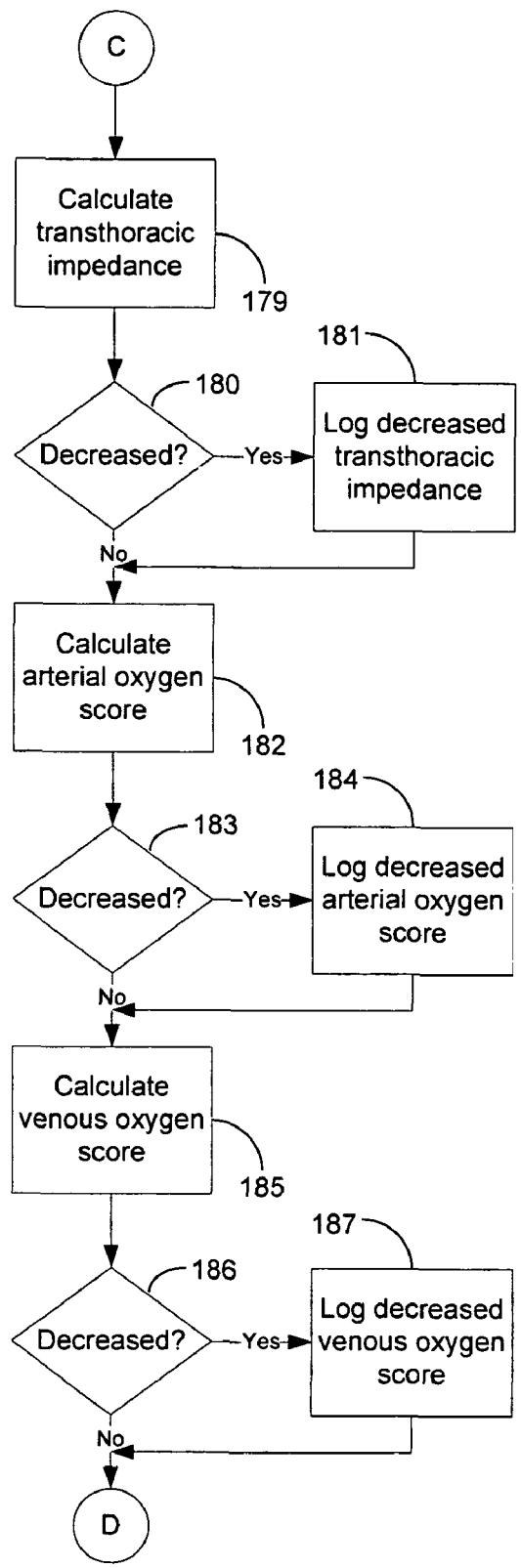
Figure 11C:
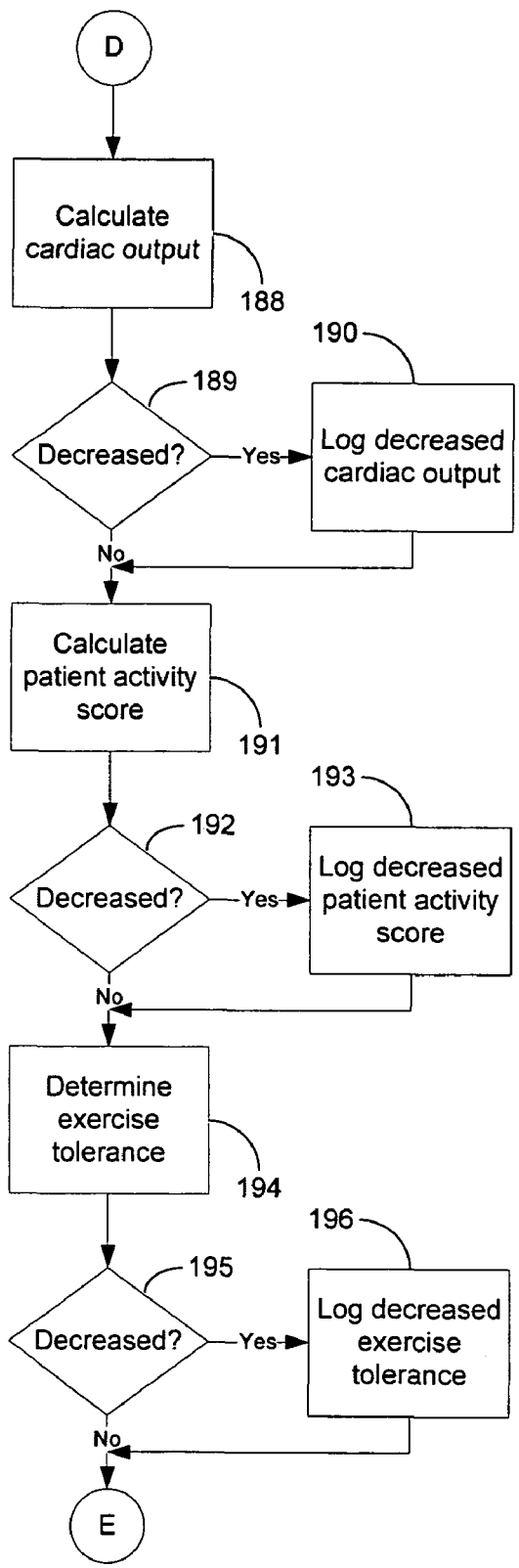
Figure 11D:
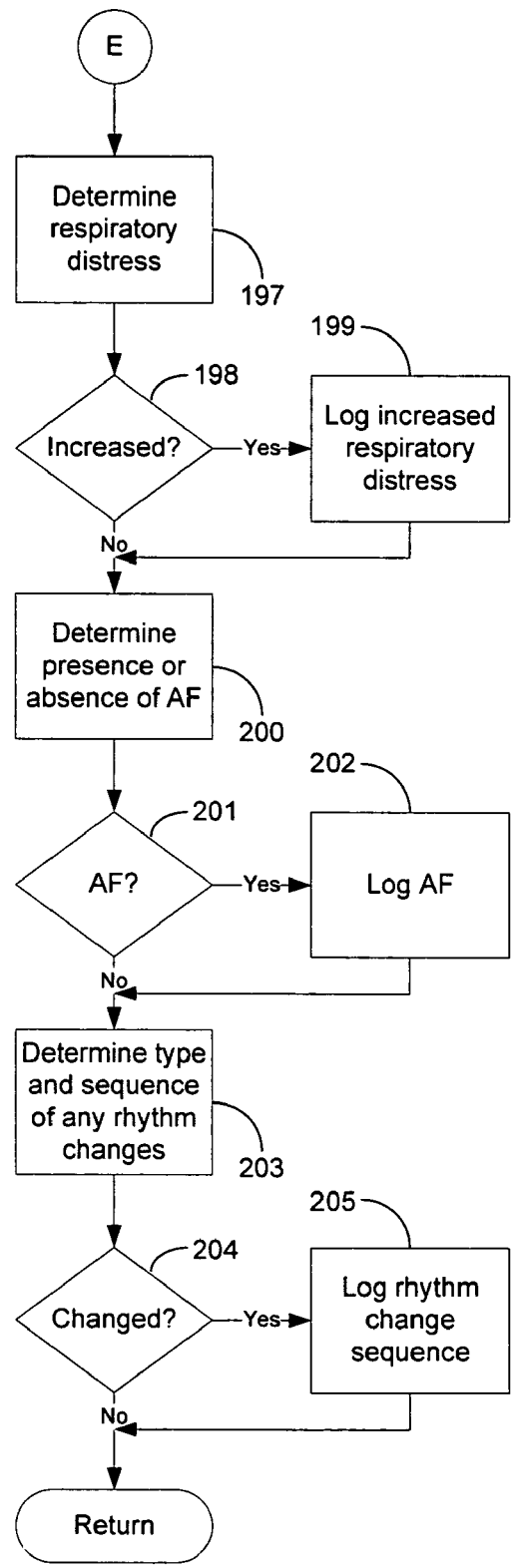

FIG. 10 is a flow diagram showing the routine for retrieving monitoring sets 138 for use in the method of FIGS. 8A-8B. The purpose of this routine is to retrieve the appropriate monitoring sets 27 from the database 17 based on the types of comparisons being performed. First, if the comparisons are self referencing with respect to the measures stored in the individual patient care record 23 (block 160), the device and derived measures set 24b and quality of life and symptom measures set 25b, if used, are retrieved for the individual patient from the database 17 (block 161). Next, if the comparisons are peer group referencing with respect to measures stored in the patient care records 23 for a health disorder- or disease-specific peer group (block 162), the device and derived measures set 24b and quality of life and symptom measures set 25b, if used, are retrieved from each patient care record 23 for the peer group from the database 17 (block 163). Data for each measure (e.g., minimum, maximum, averaged, standard deviation, and trending data) from the monitoring sets 27 for the peer group is then calculated (block 164). Finally, if the comparisons are population referencing with respect to measures stored in the patient care records 23 for the overall patient population (block 165), the device and derived measures set 24b and quality of life and symptom measures set 25b, if used, are retrieved from each patient care record 23 from the database 17 (block 166). Minimum, maximum, averaged, standard deviation, and trending data and other numerical processes using the data, as is known in the art, for each measure from the monitoring sets 27 for the peer group is then calculated (block 167). The routine then returns.

FIGS. 11A-11D are flow diagrams showing the routine for testing threshold limits 139 for use in the method of FIG. 8A and 8B. The purpose of this routine is to analyze, compare, and log any differences between the observed, objective measures stored in the reference baseline 26, if used, and the monitoring sets 27 to the indicator thresholds 129. Briefly, the routine consists of tests pertaining to each of the indicators relevant to diagnosing and monitoring congestive heart failure. The threshold tests focus primarily on: (1) changes to and rates of change for the indicators themselves, as stored in the combined device and derived measures set 95 (shown in FIG. 4) or similar data structure; and (2) violations of absolute threshold limits which trigger an alert. The timing and degree of change may vary with each measure and with the natural fluctuations noted in that measure during the reference baseline period. In addition, the timing and degree of change might also vary with the individual and the natural history of a measure for that patient.

One suitable approach to performing the threshold tests uses a standard statistical linear regression technique using a least squares error fit. The least squares error fit can be calculated as follows:

$$y = \beta_0 + \beta_1 x \tag{1}$$

$$\beta = \frac{SS_{xy}}{SS_{xx}} \tag{2}$$

$$SS_{xy} = \sum_{i=1}^{n} x_i y_i - \frac{\left(\sum_{i=1}^{n} x_i\right)\left(\sum_{i=1}^{n} y_i\right)}{n} \tag{3}$$

$$SS_{xx} = \sum_{i=1}^{n} x_i^2 - \frac{\left(\sum_{i=1}^{n} x_i\right)^2}{n} \tag{4}$$

where n is the total number of measures, $x_i$ is the time of day for measure i, and $y_i$ is the value of measure i, $\beta_1$ is the slope, and $\beta_0$ is the y-intercept of the least squares error line. A positive slope $\beta_1$ indicates an increasing trend, a negative slope $\beta_1$ indicates a decreasing trend, and no slope indicates no change in patient condition for that particular measure. A predicted measure value can be calculated and compared to the appropriate indicator threshold 129 for determining whether the particular measure has either exceeded an acceptable threshold rate of change or the absolute threshold limit.

For any given patient, three basic types of comparisons between individual measures stored in the monitoring sets 27 are possible: self referencing, peer group, and general population, as explained above with reference to FIG. 6. In addition, each of these comparisons can include comparisons to individual measures stored in the pertinent reference baselines 24.

The indicator thresholds 129 for detecting a trend indicating progression into a state of congestive heart failure or a state of imminent or likely congestive heart failure, for example, over a one week time period, can be as follows:

(1) Respiratory rate (block 170): If the respiratory rate has increased over 1.0 SD from the mean respiratory rate in the reference baseline 26 (block 171), the increased respiratory rate and time span over which it occurs are logged in the combined measures set 95 (block 172).

(2) Heart rate (block 173): If the heart rate has increased over 1.0 SD from the mean heart rate in the reference baseline 26 (block 174), the increased heart rate and time span over which it occurs are logged in the combined measures set 95 (block 175).

(3) Pulmonary artery diastolic pressure (PADP) (block 176) reflects left ventricular filling pressure and is a measure of left ventricular dysfunction. Ideally, the left ventricular end diastolic pressure (LVEDP) should be monitored, but in practice is difficult to measure. Consequently, without the LVEDP, the PADP, or derivatives thereof, is suitable for use as an alternative to LVEDP in the present invention. If the PADP has increased over 1.0

SD from the mean PADP in the reference baseline 26 (block 177), the increased PADP and time span over which that increase occurs, are logged in the combined measures set 95 (block 178). Other cardiac pressures or derivatives could also apply.

(4) Transthoracic impedance (block 179): If the transthoracic impedance has decreased over 1.0 SD from the mean transthoracic impedance in the reference baseline 26 (block 180), the decreased transthoracic impedance and time span are logged in the combined measures set 95 (block 181).

(5) Arterial oxygen score (block 182): If the arterial oxygen score has decreased over 1.0 SD from the arterial oxygen score in the reference baseline 26 (block 183), the decreased arterial oxygen score and time span are logged in the combined measures set 95 (block 184).

(6) Venous oxygen score (block 185): If the venous oxygen score has decreased over 1.0 SD from the mean venous oxygen score in the reference baseline 26 (block 186), the decreased venous oxygen score and time span are logged in the combined measures set 95 (block 187).

(7) Cardiac output (block 188): If the cardiac output has decreased over 1.0 SD from the mean cardiac output in the reference baseline 26 (block 189), the decreased cardiac output and time span are logged in the combined measures set 95 (block 190).

(8) Patient activity score (block 191): If the mean patient activity score has decreased over 1.0 SD from the mean patient activity score in the reference baseline 26 (block 192), the decreased patient activity score and time span are logged in the combined measures set 95 (block 193).

(9) Exercise tolerance quality of life (QOL) measures (block 194): If the exercise tolerance QOL has decreased over 1.0 SD from the mean exercise tolerance in the reference baseline 26 (block 195), the decrease in exercise tolerance and the time span over which it occurs are logged in the combined measures set 95 (block 196).

(10) Respiratory distress quality of life (QOL) measures (block 197): If the respiratory distress QOL measure has deteriorated by more than 1.0 SD from the mean respiratory distress QOL measure in the reference baseline 26 (block 198), the increase in respiratory distress and the time span over which it occurs are logged in the combined measures set 95 (block 199).

(11) Atrial fibrillation (block 200): The presence or absence of atrial fibrillation (AF) is determined and, if present (block 201), atrial fibrillation is logged (block 202).

(12) Rhythm changes (block 203): The type and sequence of rhythm changes is significant and is determined based on the timing of the relevant rhythm measure, such as sinus rhythm. For instance, a finding that a rhythm change to atrial fibrillation precipitated circulatory measures changes can indicate therapy directions against atrial fibrillation rather than primary progression of congestive heart failure. Thus, if there are rhythm changes (block 204), the sequence of the rhythm changes and time span are logged (block 205).

Note also that an inversion of the indicator thresholds 129 defined above could similarly be used for detecting a trend in disease regression. One skilled in the art would recognize that these measures would vary based on whether or not they were recorded during rest or during activity and that the measured activity score can be used to indicate the degree of patient rest or activity. The patient activity score can be determined via an implantable motion detector, for example, as described in U.S. Pat. No. 4,428,37, issued Jan. 31, 1984, to Anderson et al., the disclosure of which is incorporated herein by reference.

The indicator thresholds 129 for detecting a trend towards a state of congestive heart failure can also be used to declare, a priori, congestive heart failure present, regardless of pre-existing trend data when certain limits are established, such as:

(1) An absolute limit of PADP (block 170) exceeding 25 mm Hg is an a priori definition of congestive heart failure from left ventricular volume overload.

(2) An absolute limit of indexed cardiac output (block 191) falling below $2.0 \text{ l/min/m}^2$ is an a priori definition of congestive heart failure from left ventricular myocardial pump failure when recorded in the absence of intravascular volume depletion (e.g., from hemorrhage, septic shock, dehydration, etc.) as indicated by a reduced PADP (e.g., <10 mmHg).

Figure 12:
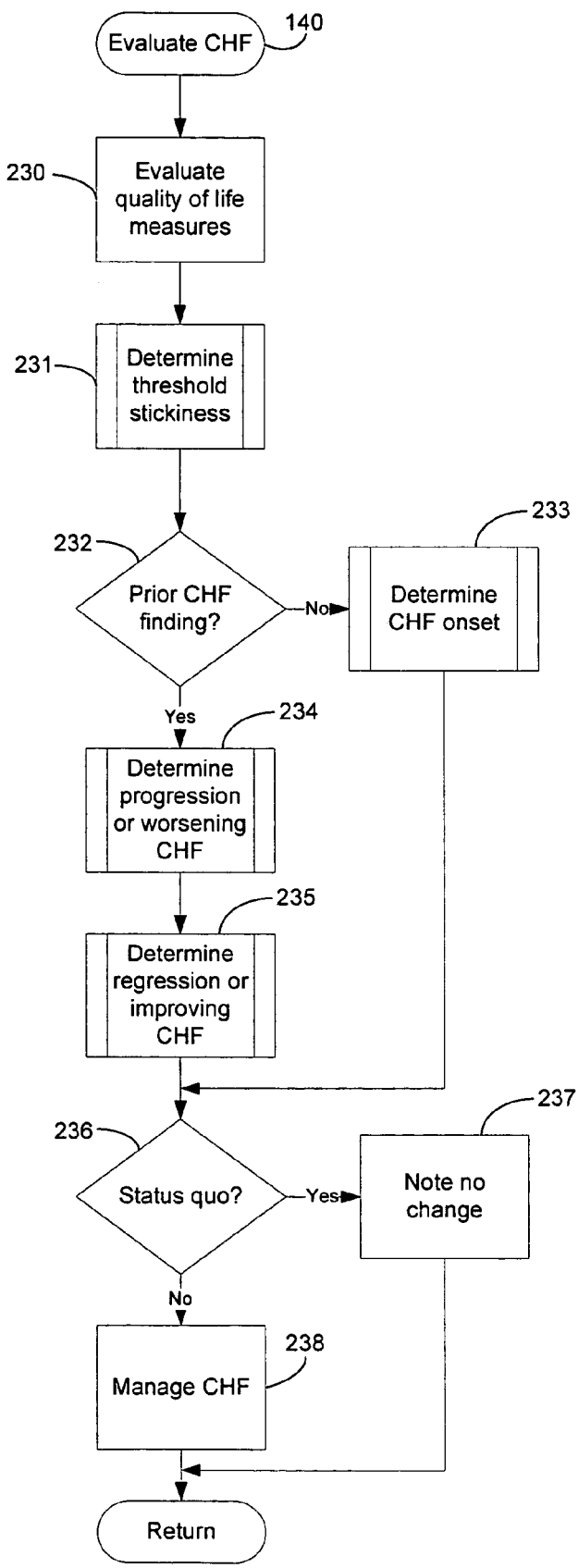
FIG. 12 is a flow diagram showing the routine for evaluating the onset, progression, regression, and status quo of congestive heart failure for use in the method of FIGS. 8A-8B.

FIG. 12 is a flow diagram showing the routine for evaluating the onset, progression, regression and status quo of congestive heart failure 140 for use in the method of FIG. 8A and 8B. The purpose of this routine is to evaluate the presence of sufficient indicia to warrant a diagnosis of the onset, progression, regression, and status quo of congestive heart failure. Quality of life and symptom measures set 25a, 25b can be included in the evaluation (block 230) by determining whether any of the individual quality of life and symptom measures set 25a, 25b have changed relative to the previously collected quality of life and symptom measures from the monitoring sets 27 and the reference baseline 26, if used. For example, an increase in the shortness of breath measure 87 and exercise tolerance measure 89 would corroborate a finding of congestive heart failure. Similarly, a transition from NYHA Class II to NYHA Class III would indicate deterioration or, conversely, a transition from NHHA Class III to NYHA Class II status would indicate improvement or progress. Incorporating the quality of life and symptom measures set 25a, 25b into the evaluation can help, in part, to refute or support findings based on physiological data. Next, a determination as to whether any changes to interventive measures are appropriate based on threshold stickiness ("hysteresis") is made (block 231), as further described below with reference to FIG. 16.

The routine returns upon either the determination of a finding or elimination of all factors as follows. If a finding of congestive heart failure was not previously diagnosed (block 232), a determination of disease onset is made (block 233), as further described below with reference to FIGS. 13A-13C. Otherwise, if congestive heart failure was previously diagnosed (block 232), a further determination of either disease progression or worsening (block 234) or regression or improving (block 235) is made, as further described below with reference to FIGS. 14A-14C and 15A-15C, respectively. If, upon evaluation, neither disease onset (block 233), worsening (block 234) or improving (block 235) is indicated, a finding of status quo is appropriate (block 236) and noted (block 235). Otherwise, congestive heart failure and the related outcomes are actively managed (block 238) through the administration of, non-exclusively, preload reduction, afterload reduction, diuresis, beta-blockade, inotropic agents, electrolyte management, electrical therapies, mechanical therapies, and other therapies as are known in the art. The management of congestive heart failure is described, by way of example, in E. Braunwald, ed., "Heart Disease—A Textbook of Cardiovascular Medicine," Ch. 17, W. B. Saunders Co. (1997), the disclosure of which is incorporated herein by reference. The routine then returns.

Figure 13A:
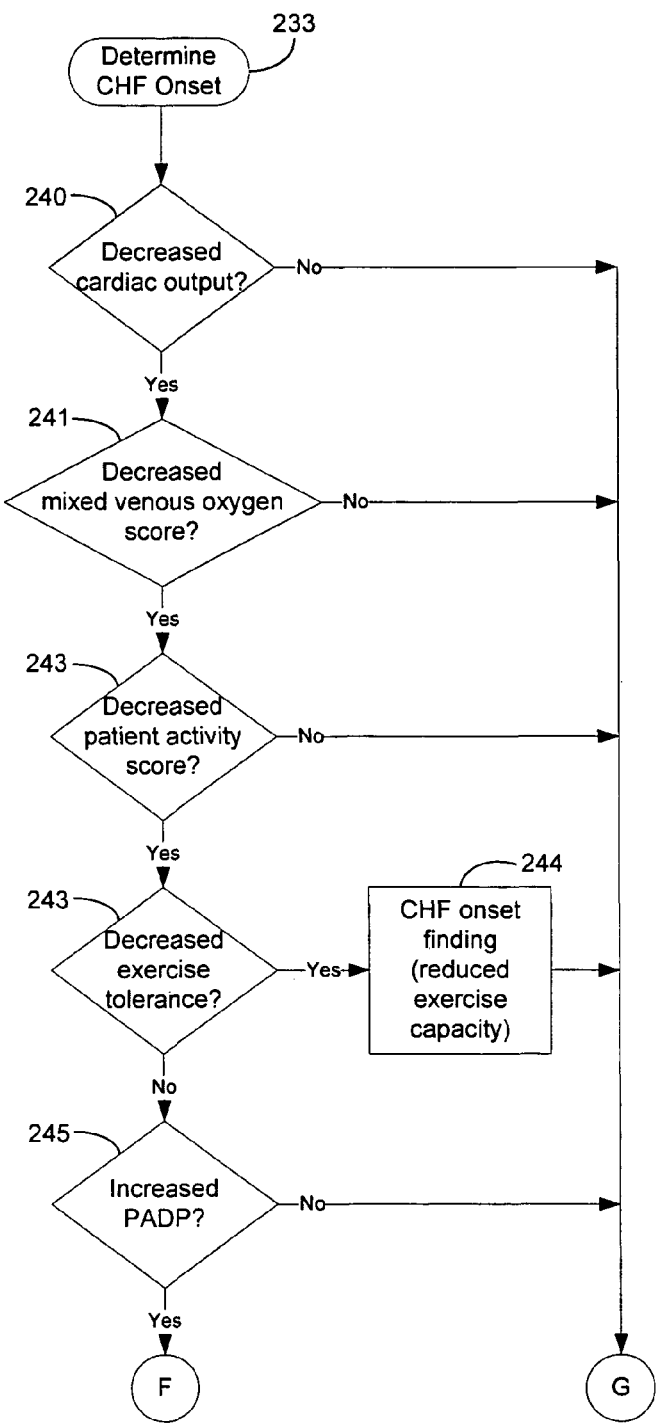
FIGS. 13A-13B are flow diagrams showing the routine for determining an onset of congestive heart failure for use in the routine of FIG. 12.
Figure 13B:
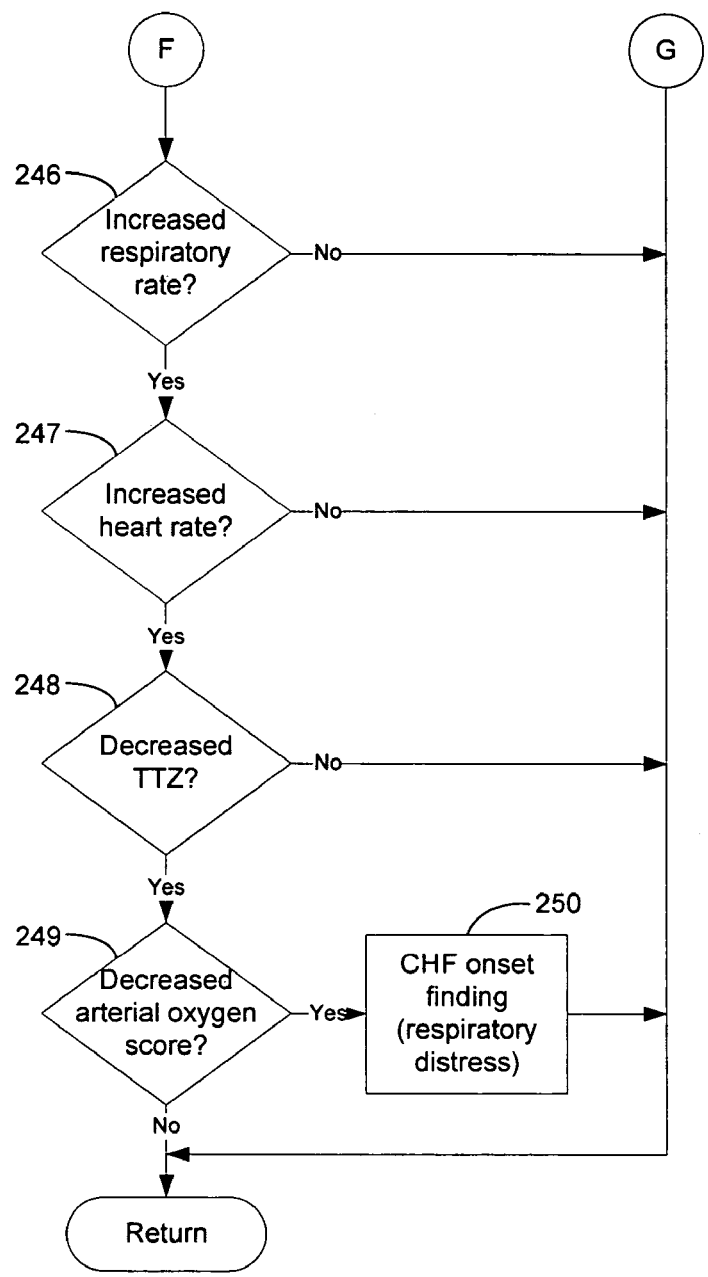

FIGS. 13A-13B are flow diagrams showing the routine for determining an onset of congestive heart failure 232 for use in the routine of FIG. 12. Congestive heart failure is possible based on two general symptom categories: reduced exercise capacity (block 244) and respiratory distress (block 250). An effort is made to diagnose congestive heart failure manifesting primarily as resulting in reduced exercise capacity (block 244) and/or increased respiratory distress (block 250). Several factors need be indicated to warrant a diagnosis of congestive heart failure onset, as well as progression, as summarized below with reference to FIGS. 13A-13B in TABLE 1, Disease Onset or Progression. Reduced exercise capacity generally serves as a marker of low cardiac output and respiratory distress as a marker of increased left ventricular end diastolic pressure. The clinical aspects of congestive heart failure are described, by way of example, in E. Braunwald, ed., "Heart Disease—A Textbook of Cardiovascular Medicine," Chs. 1 and 15, W. B. Saunders Co. (1997), the disclosure of which is incorporated herein by reference.

Per TABLE 1, multiple individual indications (blocks 240-243, 245-250) should be present for the two principal findings of congestive heart failure related reduced exercise capacity (block 244), or congestive heart failure related respiratory distress (block 250), to be indicated, both for disease onset or progression. A bold "++" symbol indicates a primary key finding which is highly indicative of congestive heart failure, that is, reduced exercise capacity or respiratory distress, a bold "+" symbol indicates a secondary key finding which is strongly suggestive, and a "±" symbol indicates a tertiary permissive finding which may be present or absent. The presence of primary key findings alone can be sufficient to indicate an onset of congestive heart failure and secondary key findings serve to corroborate disease onset. Note the presence of any abnormality can trigger an analysis for the presence or absence of secondary disease processes, such as the presence of atrial fibrillation or pneumonia. Secondary disease considerations can be evaluated using the same indications (see, e.g., blocks 141-144 of FIGS. 8A-8B), but with adjusted indicator thresholds 129 (shown in FIG. 5) triggered at a change of 0.5 SD, for example, instead of 1.0 SD.

In the described embodiment, the reduced exercise capacity and respiratory distress findings (blocks 244, 250) can be established by consolidating the individual indications (blocks 240-243, 245-250) in several ways. First, in a preferred embodiment, each individual indication (blocks 240-243, 245-250) is assigned a scaled index value correlating with the relative severity of the indication. For example, decreased cardiac output (block 240) could be measured on a scale from '1' to '5' wherein a score of '1' indicates no change in cardiac output from the reference point, a score of '2' indicates a change exceeding 0.5 SD, a score of '3' indicates a change exceeding 1.0 SD, a score of '4' indicates a change exceeding 2.0 SD, and a score of '5' indicates a change exceeding 3.0 SD.

The index value for each of the individual indications (blocks 240-243, 245-250) can then either be aggregated or averaged with a result exceeding the aggregate or average maximum indicating an appropriate congestive heart failure finding.

Preferably, all scores are weighted depending upon the assignments made from the measures in the reference baseline 26. For instance, transthoracic impedance 104 (shown in FIG. 4) could be weighted more importantly than respiratory rate 103 if the respiratory rate in the reference baseline 26 is particularly high at the outset, making the detection of further disease progression from increases in respiratory rate, less sensitive. In the described embodiment, cardiac output 100 receives the most weight in determining a reduced exercise capacity finding whereas pulmonary artery diastolic pressure 99 receives the most weight in determining a respiratory distress or dyspnea finding.

Alternatively, a simple binary decision tree can be utilized wherein each of the individual indications (blocks 240-243, 245-250) is either present or is not present. All or a majority of the individual indications (blocks 240-243, 245-250) should be present for the relevant congestive heart failure finding to be affirmed.

Other forms of consolidating the individual indications (blocks 240-243, 245-250) are feasible.

Figure 14A:
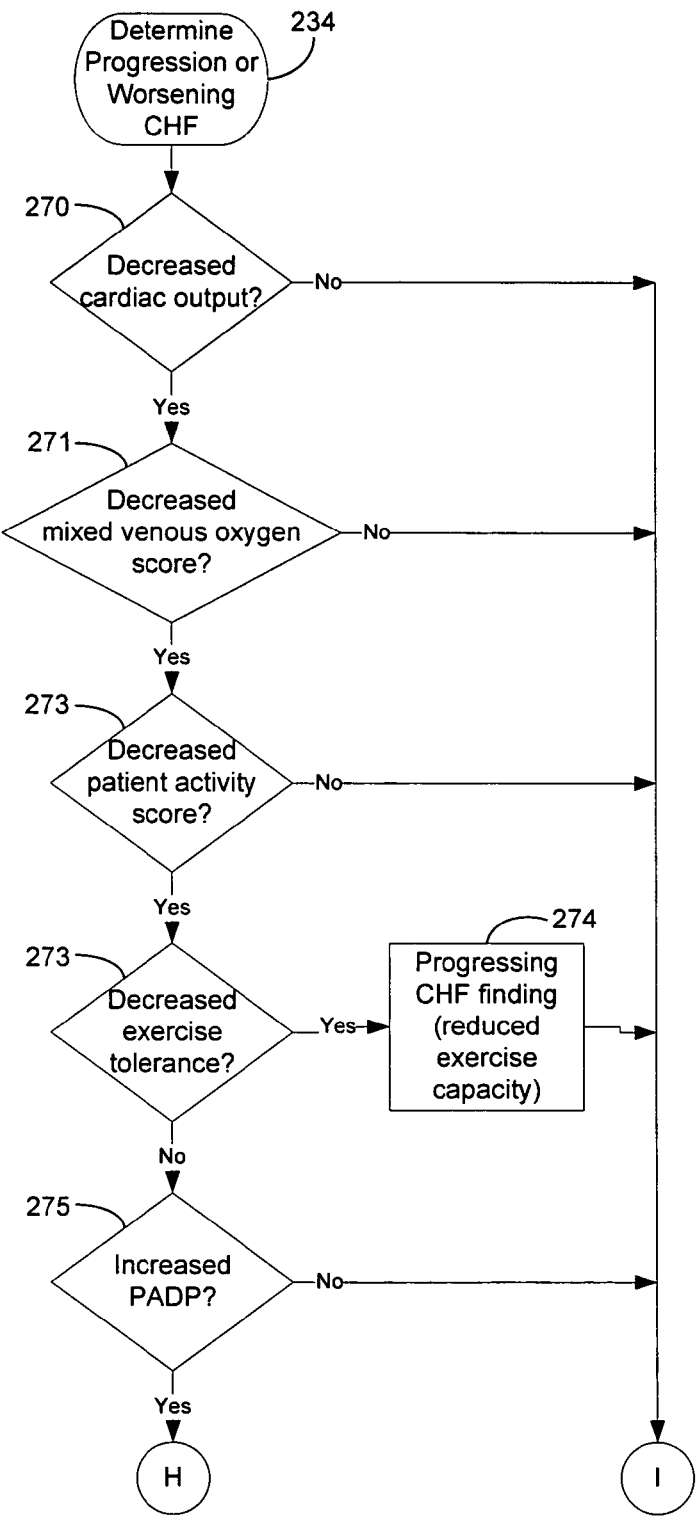
FIGS. 14A-14B are flow diagrams showing the routine for determining progression or worsening of congestive heart failure for use in the routine of FIG. 12.
Figure 14B:
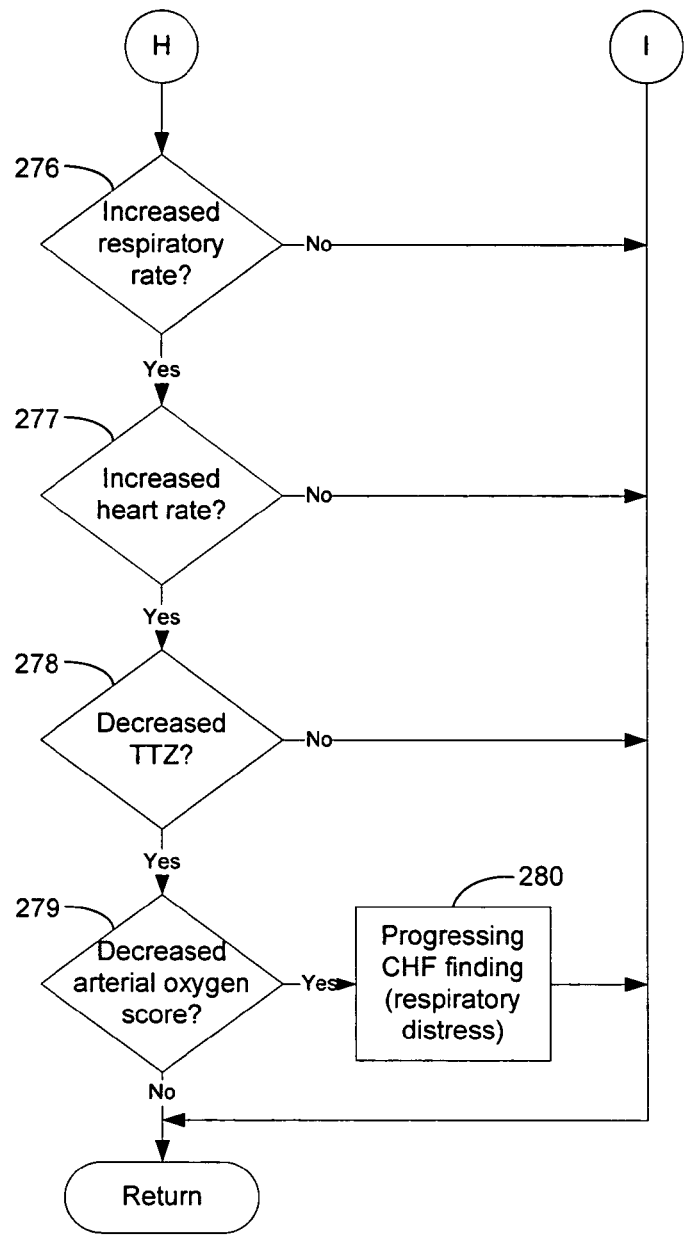

FIGS. 14A-14B are flow diagrams showing the routine for determining a progression or worsening of congestive heart failure 233 for use in the routine of FIG. 12. The primary difference between the determinations of disease onset, as described with reference to FIGS. 13A-13B, and disease progression is the evaluation of changes indicated in the same factors present in a disease onset finding. Thus, a revised congestive heart failure finding is possible based on the same two general symptom categories: reduced exercise capacity (block 264) and respiratory distress (block 271). The same factors which need be indicated to warrant a diagnosis of congestive heart failure onset are evaluated to determine disease progression, as summarized below with reference to FIGS. 14A-14B in TABLE 1, Disease Onset or Progression.

Figure 15A:
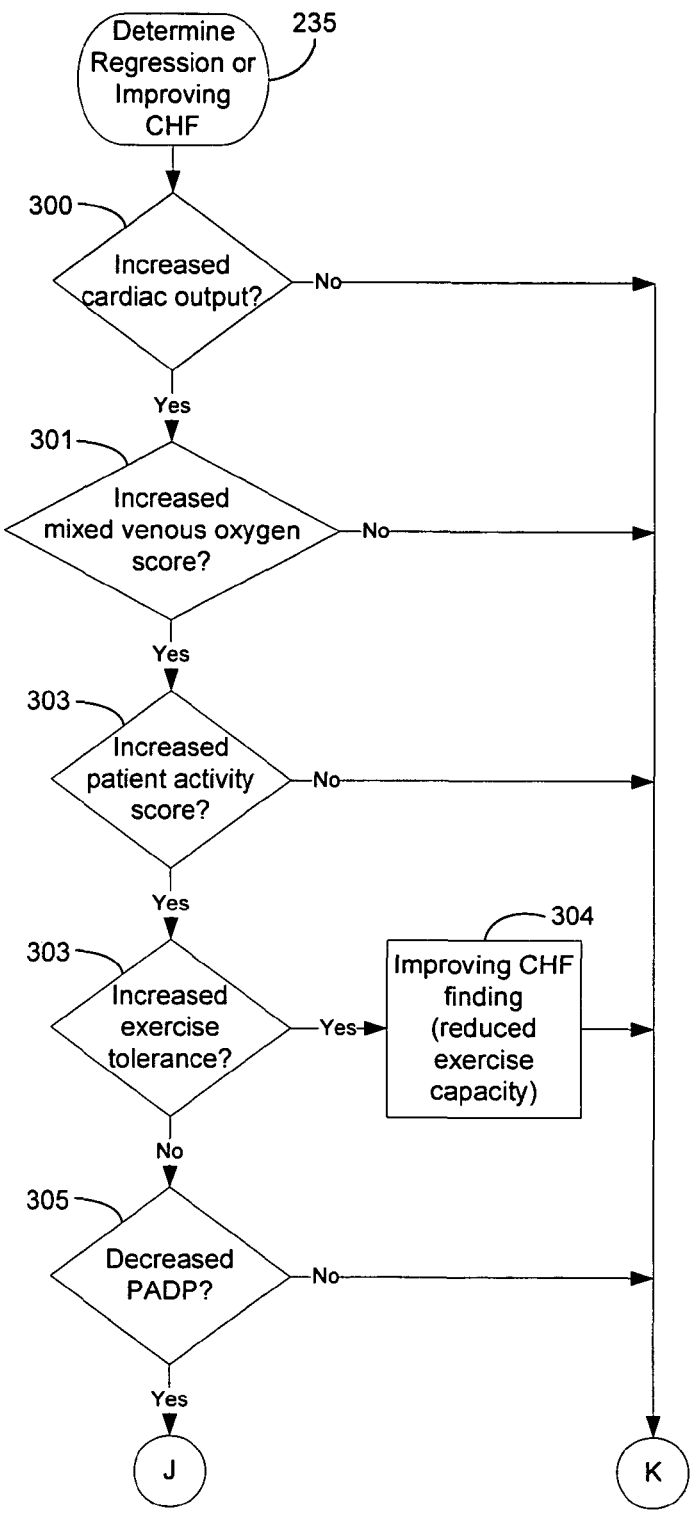
FIGS. 15A-15B are flow diagrams showing the routine for determining regression or improving of congestive heart failure for use in the routine of FIG. 12.
Figure 15B:
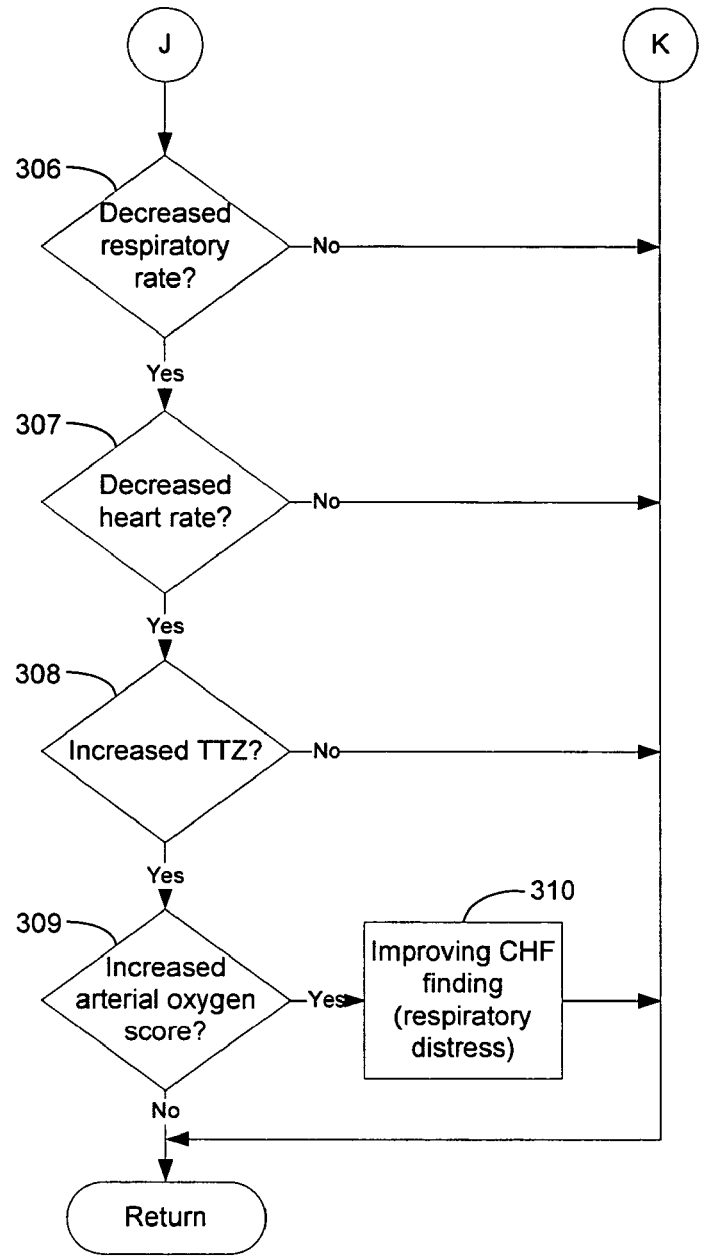

Similarly, these same factors trending in opposite directions from disease onset or progression, are evaluated to determine disease regression or improving, as summarized below with reference to FIGS. 15A-15B in TABLE 2, Disease Regression. Per TABLE 2, multiple individual indications (blocks 260-263, 265-270) should be present for the two principal findings of congestive heart failure related reduced exercise capacity (block 264), or congestive heart failure related respiratory distress (block 271), to indicate disease regression. As in TABLE 1, a bold "++" symbol indicates a primary key finding which is highly indicative of congestive heart failure, that is, reduced exercise capacity or respiratory distress, a bold "+" symbol indicates a secondary key finding which is strongly suggestive, and a "±" symbol indicates a tertiary permissive finding which may be present or absent. The more favorable the measure, the more likely regression of congestive heart failure is indicated.

Figure 16:
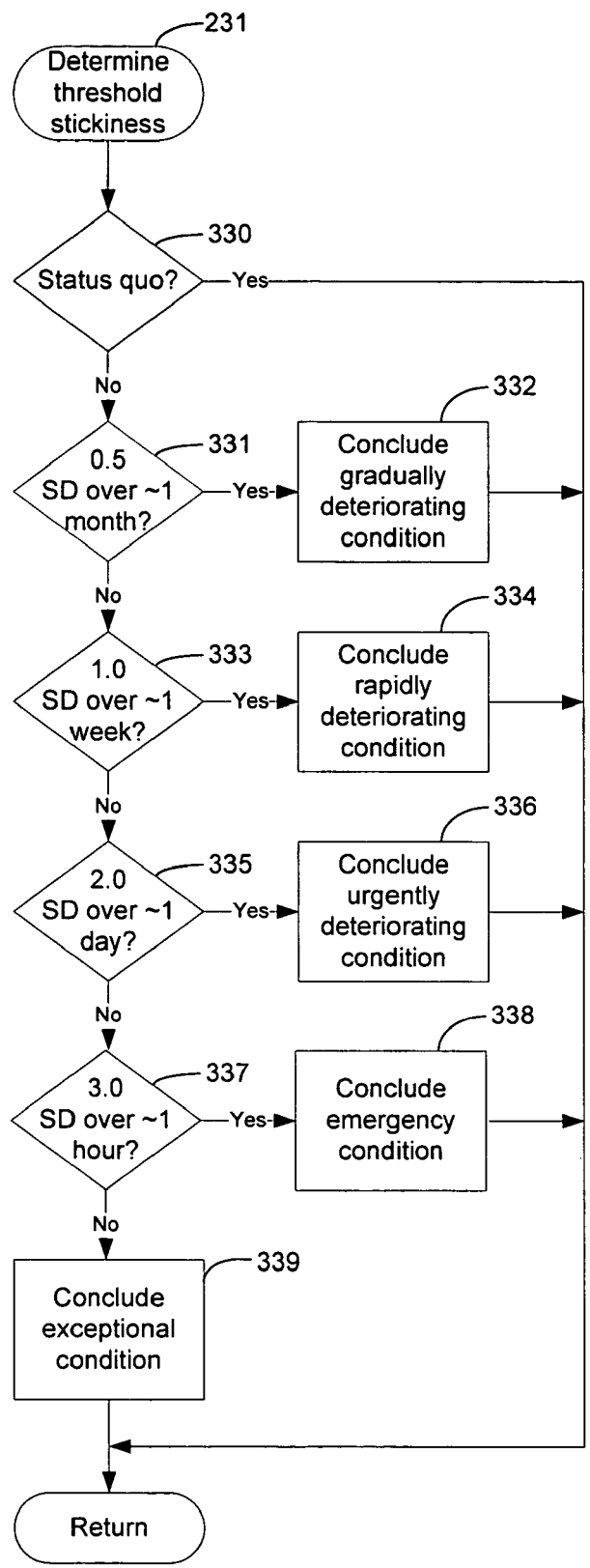
FIG. 16 is a flow diagram showing the routine for determining threshold stickiness ("hysteresis") for use in the method of FIG. 12.

FIG. 16 is a flow diagram showing the routine for determining threshold stickiness ("hysteresis") 231 for use in the method of FIG. 12. Stickiness, also known as hysteresis, is a medical practice doctrine whereby a diagnosis or therapy will not be changed based upon small or temporary changes in a patient reading, even though those changes might temporarily move into a new zone of concern. For example, if a patient measure can vary along a scale of '1' to '10' with '10' being worse, a transient reading of '6,' standing alone, on a patient who has consistently indicated a reading of '5' for weeks will not warrant a change in diagnosis without a definitive prolonged deterioration first being indicated. Stickiness dictates that small or temporary changes require more diagnostic certainty, as confirmed by the persistence of the changes, than large changes would require for any of the monitored (device) measures. Stickiness also makes reversal of important diagnostic decisions, particularly those regarding life-threatening disorders, more difficult than reversal of diagnoses of modest import. As an example, automatic external defibrillators (AEDs) manufactured by Heartstream, a subsidiary of Agilent Technologies, Seattle, Wash., monitor heart rhythms and provide interventive shock treatment for the diagnosis of ventricular fibrillation. Once diagnosis of ventricular fibrillation and a decision to shock the patient has been made, a pattern of no ventricular fibrillation must be indicated for a relatively prolonged period before the AED changes to a "no-shock" decision. As implemented in this AED example, stickiness mandates certainty before a decision to shock is disregarded.

In practice, stickiness also dictates that acute deteriorations in disease state are treated aggressively while chronic, more slowly progressing disease states are treated in a more tempered fashion. Thus, if the patient status indicates a status quo (block 330), no changes in treatment or diagnosis are indicated and the routine returns. Otherwise, if the patient status indicates a change away from status quo (block 330), the relative quantum of change and the length of time over which the change has occurred is determinative. If the change of approximately 0.5 SD has occurred over the course of about one month (block 331), a gradually deteriorating condition exists (block 332) and a very tempered diagnostic, and if appropriate, treatment program is undertaken. If the change of approximately 1.0 SD has occurred over the course of about one week (block 333), a more rapidly deteriorating condition exists (block 334) and a slightly more aggressive diagnostic, and if appropriate, treatment program is undertaken. If the change of approximately 2.0 SD has occurred over the course of about one day (block 335), an urgently deteriorating condition exists (block 336) and a moderately aggressive diagnostic, and if appropriate, treatment program is undertaken. If the change of approximately 3.0 SD has occurred over the course of about one hour (block 337), an emergency condition exists (block 338) and an immediate diagnostic, and if appropriate, treatment program is undertaken as is practical. Finally, if the change and duration fall outside the aforementioned ranges (blocks 331-338), an exceptional condition exists (block 339) and the changes are reviewed manually, if necessary. The routine then returns. These threshold limits and time ranges may then be adapted depending upon patient history and peer-group guidelines.

The form of the revised treatment program depends on the extent to which the time span between changes in the device measures exceed the threshold stickiness 133 (shown in FIG. 5) relating to that particular type of device measure. For example, threshold stickiness 133 indicator for monitoring a change in heart rate in a chronic patient suffering from congestive heart failure might be 10% over a week. Consequently, a change in average heart rate 96 (shown in FIG. 4) from 80 bpm to 95 bpm over a seven day period, where a 14 beat per minute average change would equate to a 1.0 SD change, would exceed the threshold stickiness 133 and would warrant a revised medical diagnosis perhaps of disease progression. One skilled in the art would recognize the indications of acute versus chronic disorders which will vary upon the type of disease, patient health status, disease indicators, length of illness, and timing of previously undertaken interventive measures, plus other factors.

The present invention provides several benefits. One benefit is improved predictive accuracy from the outset of patient care when a reference baseline is incorporated into the automated diagnosis. Another benefit is an expanded knowledge base created by expanding the methodologies applied to a single patient to include patient peer groups and the overall patient population. Collaterally, the information maintained in the database could also be utilized for the development of further predictive techniques and for medical research purposes. Yet a further benefit is the ability to hone and improve the predictive techniques employed through a continual reassessment of patient therapy outcomes and morbidity rates.

Other benefits include an automated, expert system approach to the cross-referral, consideration, and potential finding or elimination of other diseases and health disorders with similar or related etiological indicators and for those other disorders that may have an impact on congestive heart failure. Although disease specific markers will prove very useful in discriminating the underlying cause of symptoms, many diseases, other than congestive heart failure, will alter some of the same physiological measures indicative of congestive heart failure. Consequently, an important aspect of considering the potential impact of other disorders will be, not only the monitoring of disease specific markers, but the sequencing of change and the temporal evolution of more general physiological measures, for example respiratory rate, arterial oxygenation, and cardiac output, to reflect disease onset, progression or regression in more than one type of disease process.

While the invention has been particularly shown and described as referenced to the embodiments thereof, those skilled in the art will understand that the foregoing and other changes in form and detail may be made therein without departing from the spirit and scope of the invention.

TABLE 1

Disease Onset or Progression.

| Individual Indications | Congestive Heart Failure (Reduced Exercise Capacity) Finding (block 244, 274) | Congestive Heart Failure (Increasing Respiratory Distress) Finding (block 250, 280) |
| --- | --- | --- |
| Decreased cardiac output (blocks 240, 260) | ++ | ± |
| Decreased mixed venous oxygen score (blocks 241, 261) | + | ± |
| Decreased patient activity score (block 243, 263) | + | ± |
| Increased pulmonary artery diastolic pressure (PADP) (block 245, 265) | ± | ++ |
| Increased respiratory rate (block 246, 266) | ± | + |
| Decreased transthoracic impedance (TTZ) (block 248, 268) | ± | + |

TABLE 2

Disease Regression.

| Individual Indications | Congestive Heart Failure (Improving Exercise Capacity) Finding (block 304) | Congestive Heart Failure (Decreasing Respiratory Distress) Finding (block 310) |
| --- | --- | --- |
| Increased cardiac output (block 300) | ++ | ± |
| Increased mixed venous oxygen score (block 301) | + | ± |
| Increased patient activity score (block 303) | + | ± |
| Decreased pulmonary artery diastolic pressure (PADP) (block 305) | ± | ++ |
| Decreased respiratory rate (block 306) | ± | + |
| Increased transthoracic impedance (TTZ) (block 308) | ± | + |

What is claimed is:

1. An analysis system for processing physiometry for use in remote automated congestive heart failure patient management, comprising:
   a medical device;
   one or more patient records, wherein each patient record comprises:
      information to identify a patient enrolled in automated patient care and comprising at least one of treatment profile and medical history;
      collected device measures to provide raw physiometry for the patient that was regularly monitored and recorded by a the medical device; and
      derived device measures calculated from the collected device measures to provide derivative physiometry;
   a database configured to store the one or more patient records;
   an interface configured to periodically receive the collected device measures;
   a processing module, comprising:
      a data processor configured to calculate the derived device measures; and
      an analyzer configured to evaluate the collected and derived device measures and to quantify a pathophysiology indicative of congestive heart failure; and
   hysteresis parameters to temporally define a threshold for changes in the pathophysiology, wherein the analyzer further analyzes the hysteresis parameters against one or more of the collected and derived device measures and determines an indicator of patient status from said analysis, wherein the hysteresis parameters allow said determination to not be changed upon temporary changes but upon the persistence of the change.

2. An analysis system according to claim 1, further comprising:
   evaluation parameters configured to define a threshold for the pathophysiology in terms of at least one of a cardiovascular and cardiopulmonary disease; and
   the indicator of patient status determined by the analyzer, wherein the analyzer analyzes one or more of the collected and derived device measures against the evaluation parameters.

3. An analysis system according to claim 2, further comprising:
   a patient status determined by the analyzer, wherein the analyzer evaluates a plurality of the indicators of patient status to identify at least one of a change and a status quo of congestive heart failure.

4. An analysis system according to claim 1, wherein each patient care record further comprises a remote client processing voice feedback into a set of quality of life measures, the voice feedback having been spoken by the patient substantially contemporaneous to the recordation of the collected device measures.

5. An analysis system according to claim 1, wherein one or more of the collected and derived device measures are selected from the group comprising self referencing, peer group, and general population physiometric measures.

6. An analysis system according to claim 1, further comprising:
   programming parameters for the medical device, wherein the collected device measures are recorded subsequent to application of the programming parameters.

7. An analysis system according to claim 1, wherein the medical device comprises one of an implantable medical device and an external medical device.

8. A method for processing physiometry for use in remote automated congestive heart failure patient management, comprising:
   regularly monitoring and recording collected device measures with a medical device;
   storing patient records into a database, wherein the patient records each comprise:
      information to identify a patient enrolled in automated patient care and comprising at least one of treatment profile and medical history;
      collected device measures to provide raw physiometry for the patient; and
      derived device measures based on the collected device measures to provide derivative physiometry;
   periodically receiving the collected device measures with an interface; and
   using a data processor to determine derived device;
   using an analyzer to evaluate the collected and derived device measures;
   specifying hysteresis parameters to temporally define a threshold for changes in the pathophysiology;
   further determining an indicator of patient status by analyzing one or more of the collected and derived device measures against the hysteresis parameters; and
   quantifying a pathphysiology indicative of congestive heath failure, wherein the hysteresis parameters allow said determination to not be changed upon temporary changes but upon the persistence of the change.

9. A method according to claim 8, further comprising:
   specifying evaluation parameters to define a threshold for the pathophysiology in terms of at least one of a cardiovascular and cardiopulmonary disease; and
   determining the indicator of patient status by analyzing one or more of the collected and derived device measures against the evaluation parameters.

10. A method according to claim 9, further comprising:
    determining a patient status comprising evaluating a plurality of the indicators of patient status and identifying at least one of a change and a status quo of congestive heart failure.

11. A method according to claim 8, further comprising:
    receiving quality of life measures, wherein the quality of life measures are in the form of voice feedback having been spoken by the patient contemporaneous to recordation of the collected device measures.

12. A method according to claim 8, wherein one or more of the collected and derived device measures are selected from the group comprising self referencing, peer group, and general population physiometric measures.

13. A method according to claim 8, further comprising:
    generating reprogramming parameters for the medical device, wherein the collected device measures are recorded subsequent to application of the reprogramming parameters.

14. A method according to claim 8, wherein the medical device comprises one of an implantable medical device and an external medical device.

15. The method according to claim 8, wherein the medical device comprises an implantable medical device.

16. An analysis system for processing physiometry for use in remote automated congestive heart failure patient management, comprising:
    an implantable medical device;
    one or more patient records, wherein each patient record comprises:

information to identify a patient enrolled in automated patient care and comprising at least one of treatment profile and medical history;

collected device measures to provide raw physiometry for the patient that was regularly monitored and recorded by the medical device; and derived device measures calculated from the collected device measures to provide derivative physiometry;

a database configured to store the one or more patient records;

an interface configured to periodically receive the collected device measures;

a processing module, comprising:

a data processor configured to calculate the derived device measures; and an analyzer configured to evaluate the collected and derived device measures and to quantify a pathophysiology indicative of congestive heart failure; and hysteresis parameters to temporally define a threshold for changes in the pathophysiology wherein the analyzer further analyzes the hysteresis parameters against one or more of the collected and derived device measures and determines an indicator of patient status from said analysis, wherein the hysteresis parameters allow said determination to not be changed upon temporary changes but upon the persistence of the change.

17. An analysis system according to claim 16, wherein each patient care record further comprises a remote client processing voice feedback into a set of quality of life measures, the voice feedback having been spoken by the patient substantially contemporaneous to the recordation of the collected device measures.

18. An analysis system according to claim 16, wherein one or more of the collected and derived device measures are selected from the group comprising self referencing, peer group, and general population physiometric measures.

19. An analysis system according to claim 16, further comprising:

programming parameters for the medical device, wherein the collected device measures are recorded subsequent to application of the programming parameters.

* * * * *

UNITED STATES PATENT AND TRADEMARK OFFICE
CERTIFICATE OF CORRECTION

| | | |
|---|---|---|
| PATENT NO. | : 7,972,274 B2 | Page 1 of 1 |
| APPLICATION NO. | : 10/876118 | |
| DATED | : July 5, 2011 | |
| INVENTOR(S) | : Gust H. Bardy | |

It is certified that error appears in the above-identified patent and that said Letters Patent is hereby corrected as shown below:

Col. 21, line 14, claim 1: "recorded by a the medical device" should read --recorded by the medical device--

Col. 22, line 26, claim 8: "pathphysiology" should read --pathophysiology--

Signed and Sealed this
Eighth Day of November, 2011

David J. Kappos
*Director of the United States Patent and Trademark Office*